US008792614B2

(12) United States Patent
Witten et al.

(10) Patent No.: US 8,792,614 B2
(45) Date of Patent: Jul. 29, 2014

(54) SYSTEM AND METHOD FOR RADIATION THERAPY TREATMENT PLANNING USING A MEMETIC OPTIMIZATION ALGORITHM

(76) Inventors: Matthew R. Witten, Great Neck, NY (US); Owen Clancey, New York, NY (US)

( * ) Notice: Subject to any disclaimer, the term of this patent is extended or adjusted under 35 U.S.C. 154(b) by 389 days.

(21) Appl. No.: 13/262,458

(22) PCT Filed: Mar. 31, 2010

(86) PCT No.: PCT/US2010/029445
§ 371 (c)(1),
(2), (4) Date: Oct. 12, 2011

(87) PCT Pub. No.: WO2010/120534
PCT Pub. Date: Oct. 21, 2010

(65) Prior Publication Data
US 2012/0020460 A1 Jan. 26, 2012

Related U.S. Application Data

(60) Provisional application No. 61/165,051, filed on Mar. 31, 2009, provisional application No. 61/306,243, filed on Feb. 19, 2010.

(51) Int. Cl.
*A61N 5/10* (2006.01)
*A61N 5/00* (2006.01)
*G06N 3/12* (2006.01)

(52) U.S. Cl.
CPC ............... *A61N 5/103* (2013.01); *A61N 5/1031* (2013.01); *A61N 5/1047* (2013.01); *G06N 3/126* (2013.01); *Y10S 378/901* (2013.01)
USPC ............................................. 378/65; 378/901

(58) Field of Classification Search
USPC ................................................ 378/4–20, 901
See application file for complete search history.

(56) References Cited

U.S. PATENT DOCUMENTS

| | | | |
|---|---|---|---|
| 3,783,251 | A | 1/1974 | Pavkovich |
| 3,987,281 | A | 10/1976 | Hodes |
| 4,729,099 | A | 3/1988 | Iverson et al. |
| 4,977,505 | A | 12/1990 | Pelizzari et al. |
| 5,027,818 | A | 7/1991 | Bova et al. |
| 5,197,466 | A | 3/1993 | Marchosky et al. |
| 5,205,289 | A | 4/1993 | Hardy et al. |

(Continued)

FOREIGN PATENT DOCUMENTS

WO    WO 2008016795 A1 *  2/2008

OTHER PUBLICATIONS

International Search Report for PCT/US2010/029445 dated Aug. 4, 2010. (4 pages).

(Continued)

*Primary Examiner* — Anastasia Midkiff
(74) *Attorney, Agent, or Firm* — Carter, DeLuca, Farrell & Schmidt, LLP

(57) ABSTRACT

A method for the optimization of radiation therapy treatment plans is disclosed. The disclosed method is equally-applicable to robotic radiosurgery as well as other types of radiosurgical delivery, intensity-modulated radiotherapy (IMRT), volumetric modulated arc therapy (VMAT), and three-dimensional conformal radiotherapy (3DCRT). A population-based heuristic approximation is used to perform a global search, and subsequently, a deterministic local trajectory search is employed to further refine the initial solution.

18 Claims, 23 Drawing Sheets

(56) References Cited

U.S. PATENT DOCUMENTS

| | | |
|---|---|---|
| 5,227,969 A | 7/1993 | Waggener et al. |
| 5,291,404 A | 3/1994 | Kurokawa et al. |
| 5,317,616 A | 5/1994 | Swerdloff et al. |
| 5,339,812 A | 8/1994 | Hardy et al. |
| 5,373,844 A | 12/1994 | Smith et al. |
| 5,418,827 A | 5/1995 | Deasy et al. |
| 5,458,125 A | 10/1995 | Schweikard |
| 5,485,085 A | 1/1996 | Sumanaweera et al. |
| 5,513,238 A | 4/1996 | Leber et al. |
| 5,531,520 A | 7/1996 | Grimson et al. |
| 5,560,360 A | 10/1996 | Filler et al. |
| 5,588,033 A | 12/1996 | Yeung |
| 5,602,892 A | 2/1997 | Llacer |
| 5,647,663 A | 7/1997 | Holmes |
| 5,740,225 A | 4/1998 | Nabatame |
| 5,740,802 A | 4/1998 | Nafis et al. |
| 5,748,703 A | 5/1998 | Cosman |
| 5,782,739 A | 7/1998 | Criss et al. |
| 5,792,147 A | 8/1998 | Evans et al. |
| 5,800,353 A | 9/1998 | McLaurin, Jr. |
| 5,866,914 A | 2/1999 | Jones |
| 5,871,018 A | 2/1999 | Delp et al. |
| 6,038,283 A | 3/2000 | Carol et al. |
| 6,093,141 A | 7/2000 | Mosseri et al. |
| 6,167,294 A | 12/2000 | Busch |
| 6,175,761 B1 | 1/2001 | Frandsen et al. |
| 6,192,103 B1 | 2/2001 | Wormington et al. |
| 6,200,255 B1 | 3/2001 | Yu |
| 6,226,418 B1 | 5/2001 | Miller et al. |
| 6,240,161 B1 | 5/2001 | Siochi |
| 6,240,308 B1 | 5/2001 | Hardy et al. |
| 6,260,005 B1 | 7/2001 | Yang et al. |
| 6,273,858 B1 | 8/2001 | Fox et al. |
| 6,301,329 B1 | 10/2001 | Surridge |
| 6,360,116 B1 | 3/2002 | Jackson, Jr. et al. |
| 6,385,477 B1 | 5/2002 | Werner et al. |
| 6,393,096 B1 | 5/2002 | Carol et al. |
| 6,408,107 B1 | 6/2002 | Miller et al. |
| 6,411,675 B1 | 6/2002 | Llacer |
| 6,504,899 B2 | 1/2003 | Pugachev et al. |
| 6,545,280 B2 | 4/2003 | Weinberg |
| 6,546,073 B1 | 4/2003 | Lee |
| 6,553,152 B1 | 4/2003 | Miller et al. |
| 6,560,311 B1 | 5/2003 | Shepard et al. |
| 6,611,615 B1 | 8/2003 | Christensen |
| 6,633,686 B1 | 10/2003 | Bakircioglu et al. |
| 6,661,872 B2 | 12/2003 | Bova |
| 6,714,620 B2 | 3/2004 | Caflisch et al. |
| 6,717,174 B2 | 4/2004 | Karellas |
| 6,719,683 B2 | 4/2004 | Frohlich |
| 6,792,072 B2 | 9/2004 | Erbel et al. |
| 6,826,313 B2 | 11/2004 | Robar et al. |
| 6,882,702 B2 | 4/2005 | Luo |
| 6,889,695 B2 | 5/2005 | Pankratov et al. |
| 6,895,077 B2 | 5/2005 | Karellas et al. |
| 6,953,943 B2 | 10/2005 | Yanagisawa et al. |
| 6,965,847 B2 | 11/2005 | Wessol et al. |
| 6,979,832 B2 | 12/2005 | Yanagisawa et al. |
| 7,027,557 B2 | 4/2006 | Llacer |
| 7,046,762 B2 | 5/2006 | Lee |
| 7,046,765 B2 | 5/2006 | Wong et al. |
| 7,072,705 B2 | 7/2006 | Miga et al. |
| 7,096,055 B1 | 8/2006 | Schweikard |
| 7,098,463 B2 | 8/2006 | Adamovics |
| 7,102,134 B2 | 9/2006 | Weinberg |
| 7,103,144 B2 | 9/2006 | Wong et al. |
| 7,103,145 B2 | 9/2006 | Wong et al. |
| 7,103,399 B2 | 9/2006 | Miga et al. |
| 7,120,223 B2 | 10/2006 | Nafstadius |
| 7,142,700 B2 | 11/2006 | Van Vaals |
| 7,162,008 B2 | 1/2007 | Earl et al. |
| 7,162,439 B2 | 1/2007 | Panelli |
| 7,187,792 B2 | 3/2007 | Fu et al. |
| 7,207,715 B2 | 4/2007 | Yue |
| 7,225,012 B1 | 5/2007 | Susil et al. |
| 7,227,925 B1 | 6/2007 | Mansfield et al. |
| 7,266,175 B1 | 9/2007 | Romesberg |
| 7,268,359 B2 | 9/2007 | Ma et al. |
| 7,280,863 B2 | 10/2007 | Shachar |
| 7,298,819 B2 | 11/2007 | Dooley et al. |
| 7,302,033 B2 | 11/2007 | Carrano et al. |
| 7,317,192 B2 | 1/2008 | Ma |
| 7,333,591 B2 | 2/2008 | Earl et al. |
| 7,349,730 B2 | 3/2008 | Ein-Gal |
| 7,352,370 B2 | 4/2008 | Wang et al. |
| 7,362,848 B2 | 4/2008 | Saracen et al. |
| 7,366,278 B2 | 4/2008 | Fu et al. |
| 7,369,645 B2 | 5/2008 | Lane |
| 7,391,026 B2 | 6/2008 | Trinkaus et al. |
| 7,391,849 B2 | 6/2008 | Smith |
| 7,400,755 B2 | 7/2008 | West et al. |
| 7,412,029 B2 | 8/2008 | Myles |
| 7,477,722 B2 | 1/2009 | Carrano et al. |
| 7,496,173 B2 | 2/2009 | Goldman et al. |
| 2002/0051513 A1 | 5/2002 | Pugachev et al. |
| 2002/0080915 A1 | 6/2002 | Frohlich |
| 2002/0106054 A1 | 8/2002 | Caflisch et al. |
| 2002/0122530 A1 | 9/2002 | Erbel et al. |
| 2002/0123681 A1 | 9/2002 | Zuk et al. |
| 2002/0188194 A1 | 12/2002 | Cosman |
| 2003/0068009 A1 | 4/2003 | Xing |
| 2003/0088179 A1 | 5/2003 | Seeley et al. |
| 2003/0169847 A1 | 9/2003 | Karellas et al. |
| 2004/0001569 A1 | 1/2004 | Luo |
| 2004/0071261 A1 | 4/2004 | Earl et al. |
| 2004/0101479 A1 | 5/2004 | Burbank et al. |
| 2004/0120560 A1 | 6/2004 | Robar et al. |
| 2004/0122311 A1 | 6/2004 | Cosman |
| 2004/0138556 A1 | 7/2004 | Cosman |
| 2004/0158146 A1 | 8/2004 | Mate et al. |
| 2004/0165696 A1 | 8/2004 | Lee |
| 2004/0202610 A1 | 10/2004 | Adair |
| 2004/0211917 A1 | 10/2004 | Adamovics |
| 2005/0004451 A1 | 1/2005 | Vilsmeier et al. |
| 2005/0027194 A1 | 2/2005 | Adler et al. |
| 2005/0041843 A1 | 2/2005 | Sawyer |
| 2005/0049477 A1 | 3/2005 | Fu et al. |
| 2005/0049478 A1 | 3/2005 | Kuduvalli et al. |
| 2005/0054910 A1 | 3/2005 | Tremblay et al. |
| 2005/0096515 A1 | 5/2005 | Geng |
| 2005/0096589 A1 | 5/2005 | Shachar |
| 2005/0101855 A1 | 5/2005 | Miga et al. |
| 2005/0143965 A1 | 6/2005 | Failla et al. |
| 2005/0148859 A1 | 7/2005 | Miga et al. |
| 2005/0171396 A1 | 8/2005 | Pankratov et al. |
| 2005/0207531 A1 | 9/2005 | Dempsey et al. |
| 2005/0228209 A1 | 10/2005 | Schneider et al. |
| 2005/0228255 A1 | 10/2005 | Saracen et al. |
| 2005/0234327 A1 | 10/2005 | Saracen et al. |
| 2005/0254622 A1 | 11/2005 | Lalcer |
| 2006/0025681 A1 | 2/2006 | Abovitz et al. |
| 2006/0058648 A1 | 3/2006 | Meier et al. |
| 2006/0067469 A1 | 3/2006 | Dooley et al. |
| 2006/0074299 A1 | 4/2006 | Sayeh |
| 2006/0074301 A1 | 4/2006 | Meier et al. |
| 2006/0074302 A1 | 4/2006 | Meier et al. |
| 2006/0074304 A1 | 4/2006 | Sayeh |
| 2006/0079764 A1 | 4/2006 | Wright et al. |
| 2006/0085175 A1 | 4/2006 | Hartlet et al. |
| 2006/0100509 A1 | 5/2006 | Wright et al. |
| 2006/0133572 A1 | 6/2006 | Wong et al. |
| 2006/0133573 A1 | 6/2006 | Wong et al. |
| 2006/0145088 A1 | 7/2006 | Ma |
| 2006/0170679 A1 | 8/2006 | Wang et al. |
| 2006/0173294 A1 | 8/2006 | Ein-Gal |
| 2006/0256915 A1 | 11/2006 | Otto et al. |
| 2006/0259282 A1 | 11/2006 | Failla et al. |
| 2006/0274061 A1 | 12/2006 | Wang et al. |
| 2006/0274924 A1 | 12/2006 | West et al. |
| 2006/0274925 A1 | 12/2006 | West et al. |
| 2006/0291710 A1 | 12/2006 | Wang et al. |
| 2006/0293583 A1 | 12/2006 | Saracen et al. |
| 2007/0003007 A1 | 1/2007 | Carrano et al. |
| 2007/0003011 A1 | 1/2007 | Lane |

(56) References Cited

U.S. PATENT DOCUMENTS

| | | |
|---|---|---|
| 2007/0003123 A1 | 1/2007 | Fu et al. |
| 2007/0015991 A1 | 1/2007 | Fu et al. |
| 2007/0034812 A1 | 2/2007 | Ma et al. |
| 2007/0038058 A1 | 2/2007 | West et al. |
| 2007/0064871 A1 | 3/2007 | Earl et al. |
| 2007/0071176 A1 | 3/2007 | Mail et al. |
| 2007/0078306 A1 | 4/2007 | Allison et al. |
| 2007/0081629 A1 | 4/2007 | Yin et al. |
| 2007/0100224 A1 | 5/2007 | Bova et al. |
| 2007/0116341 A1 | 5/2007 | Fu et al. |
| 2007/0156453 A1 | 7/2007 | Frielinghaus et al. |
| 2007/0189455 A1 | 8/2007 | Allison |
| 2007/0208677 A1* | 9/2007 | Goldberg et al. ............... 706/13 |
| 2007/0219445 A1 | 9/2007 | Liebschner et al. |
| 2007/0230765 A1 | 10/2007 | Wang et al. |
| 2007/0244387 A1 | 10/2007 | Rodriguez Ponce et al. |
| 2007/0286343 A1 | 12/2007 | Maciunas et al. |
| 2008/0004845 A1 | 1/2008 | Failla et al. |
| 2008/0008291 A1 | 1/2008 | Alakuijala et al. |
| 2008/0018643 A1 | 1/2008 | Feilkas et al. |
| 2008/0031406 A1 | 2/2008 | Yan et al. |
| 2008/0037705 A1 | 2/2008 | Carrano et al. |
| 2008/0037843 A1 | 2/2008 | Fu et al. |
| 2008/0049897 A1 | 2/2008 | Molloy |
| 2008/0069422 A1 | 3/2008 | Wang et al. |
| 2008/0081991 A1 | 4/2008 | West et al. |
| 2008/0089566 A1 | 4/2008 | Node-Langlois et al. |
| 2008/0091388 A1 | 4/2008 | Failla et al. |
| 2008/0097187 A1 | 4/2008 | Gielen et al. |
| 2008/0097195 A1 | 4/2008 | Urquhart et al. |
| 2008/0109013 A1 | 5/2008 | Fu et al. |
| 2008/0123922 A1 | 5/2008 | Gielen et al. |
| 2008/0130825 A1 | 6/2008 | Fu et al. |
| 2008/0140063 A1 | 6/2008 | Miller et al. |
| 2008/0144776 A1 | 6/2008 | Main et al. |
| 2008/0167547 A1 | 7/2008 | Bova et al. |
| 2008/0177280 A1 | 7/2008 | Adler et al. |
| 2008/0183648 A1* | 7/2008 | Goldberg et al. ............... 706/13 |
| 2008/0192892 A1 | 8/2008 | Dilmanian et al. |
| 2008/0192893 A1 | 8/2008 | Gertner |
| 2008/0202200 A1 | 8/2008 | West |
| 2008/0212738 A1 | 9/2008 | Gertner et al. |
| 2008/0214933 A1 | 9/2008 | Von Busch et al. |
| 2008/0219402 A1 | 9/2008 | Wu |
| 2008/0219405 A1 | 9/2008 | Falco et al. |
| 2008/0225044 A1 | 9/2008 | Huang et al. |
| 2008/0226030 A1 | 9/2008 | Otto |
| 2008/0228104 A1 | 9/2008 | Uber et al. |
| 2008/0242969 A1 | 10/2008 | Sayeh et al. |
| 2008/0247510 A1 | 10/2008 | Gertner et al. |
| 2008/0247622 A1 | 10/2008 | Aylward et al. |
| 2008/0255544 A1 | 10/2008 | Gielen et al. |
| 2008/0269568 A1 | 10/2008 | Lewis et al. |
| 2008/0269588 A1 | 10/2008 | Csavoy et al. |
| 2008/0269599 A1 | 10/2008 | Csavoy et al. |
| 2008/0269600 A1 | 10/2008 | Csavoy et al. |
| 2008/0269602 A1 | 10/2008 | Csavoy et al. |
| 2008/0279438 A1 | 11/2008 | West et al. |
| 2008/0292194 A1 | 11/2008 | Schmidt et al. |
| 2008/0310590 A1 | 12/2008 | Meyer et al. |
| 2009/0003525 A1 | 1/2009 | Gertner et al. |
| 2009/0003532 A1 | 1/2009 | Weber |
| 2009/0003975 A1 | 1/2009 | Kuduvalli et al. |
| 2009/0022274 A1 | 1/2009 | Gertner et al. |
| 2009/0034812 A1 | 2/2009 | Nowinski et al. |
| 2009/0041188 A1 | 2/2009 | Keall et al. |
| 2009/0041189 A1 | 2/2009 | Allison |
| 2009/0048506 A1 | 2/2009 | Fong-Ichimura et al. |
| 2009/0052610 A1 | 2/2009 | Parel et al. |

OTHER PUBLICATIONS

Li, Yongjie et al., Automatic Beam Angle Selection in IMRT Planning Using Genetic Algorithm, Phys. Med. Biol., 2004, vol, 49, No. 10, pp. 1915-1932.

* cited by examiner

Pseudocode Overview

| | |
|---|---|
| 1 | Initialize: Generate the initial problem-specific population |
| 2 | Evolve the Population |
| 3 |     While (Termination Conditions are not satisfied) |
| 4 |         Specific: Apply problem-specific operators |
| 5 |         Cultural: Apply cultural memes |
| 6 |         Evaluate: Calculate the Fitness Scores of Individuals |
| 7 |         Elite: ☐ best individuals survive to the next generation |
| 8 |         Selection: Select parents based upon fitness |
| 9 |         Local: ☐ fraction of the parents |
| 10 |             - Proceed with local memes |
| 11 |             - Use Lamarckian Learning to create offspring. |
| 12 |         Global: All parents after local improvements |
| 13 |             - Apply population operators to create offspring |
| 14 |             - No offspring selection pressure |
| 15 |     End While |
| 16 | Locally Refine the Best Individual |
| 17 |     While (Termination Conditions are not satisfied) |
| 18 |         Best Individual: Apply Conjugate Gradient |
| 19 |     End While |
| 20 | End |

FIG. 3

Beam Geometry and Dosimetric Parameters a. Totality of beams consists of all possible beams given the hardware constraints of the modality.

b. For the totality of beams, calculate the following geometry for each beam using a ray-tracing algorithm along the beam's geometrical central axis:

i. Source to Axis Distance (SAD) – the Euclidian distance from the origin of the radiation to the point of calculation.
        ii. Depth – distance from surface intersection point to the point of calculation
        iii. Off-Axis Distance (OAD) – distance in the plane perpendicular to the beam central axis to the point of calculation scaled back to a nominal SAD.

c. Calculate the dose deposition coefficients from beam geometry and measured data for a particular treatment machine. One method which may be utilized is the Khan method for dose calculation.

$$DDC = OF \times \left(\frac{SAD}{F}\right)^2 \times TPR \times OCR$$

DDC = Dose Deposition Coefficient
OF = Output Factor
TPR = Tissue-Phantom Ratio
OCR = Off-Center Ratio
F = Source-to-Calibration Point Distance d. To calculate Dose per beam, multiply the beam weight (MU) by DDC.

e. Alternatively, Monte Carlo or other model based dose calculation algorithms may be employed.

FIG. 4

Geometric Point Representation Component a. Points are generated on the boundary of the target or critical organ from the contour set.

b. Additionally, points are randomly selected inside the volume.

c. Representation of the target and the OARs by the points is not static throughout the optimization. Using the process of dynamic point sampling, the number of points changes according to a prescribed functional dependence. As the number of iterations increases, the number of optimization points in a given volume of interest changes.

FIG. 5

Fitness/Objective/Cost Function a. The formula used:

$$F_{fit}(\vec{x},\vec{w},\vec{d},\vec{v}) = \Theta(v_{t,min} - v_{p,min})w_{t,min}\sum_{1}^{n_t}\Theta\left(\delta_{thres,min} - \sum_{1}^{b}DDC_{ij}x_j\right)\left(\sum_{1}^{b}DDC_{ij}x_j - d_{p,min}\right)^2$$

$$+ \Theta(v_{t,max} - v_{p,max})w_{t,max}\sum_{1}^{n_t}\Theta\left(\sum_{1}^{b}DDC_{ij}x_j - \delta_{thres,max}\right)\left(\sum_{1}^{b}DDC_{ij}x_j - d_{p,max}\right)^2$$

$$+ \sum_{l=1}^{org}\left[\sum_{m=1}^{c_{lm}}\left[\Theta(v_{lm} - v_{p,lm})\right]w_{lm}\sum_{1}^{n_l}\Theta\left(\sum_{1}^{b}DDC_{kj}x_j - \delta_{thres,lm}\right)\left(\sum_{1}^{b}DDC_{kj}x_j - d_{p,lm}\right)^2\right]$$

*Where:*

$F_{fit}$ is the Fitness/Objective/Cost function.

x is a vector of beam weights (independent variables.)

w is a vector of constraint weights.

d is a vector of doses associated with user selected dose volume constraints.

v is a vector of volumes associated with user selected dose volume constraints.

$\Theta$ is the Heaviside function defined to be zero when the argument is less than zero, otherwise one.

Subscript t refers to target.

Subscript p refers to target prescription dose.

$n_t$ is the number of points calculated within the target.

b is the number of beam weights.

org is the number of critical organs.

$c_{lm}$ is the $m^{th}$ constraints for the $l^{th}$ critical organ.

$n_l$ is the number of points in the $l^{th}$ critical organ.

$\delta_{thres,min}$ is the dose to that point in the target such that when all points in the target are sorted, points for which the dose is less than or equal to $\delta_{thres,min}$ cause the minimum dose volume constraint for the target to be violated.

FIG. 6A

$\delta_{thres,max}$ is the dose to that point in the target such that when all point in the target are sorted, points for which the dose is greater than or equal to $\delta_{thres,max}$ cause the maximum dose volume constraint for the target to be violated.

$\delta_{thres,lm}$ is the dose to that point in the $l^{th}$ critical organ such that when all points in the organ are sorted, points for which the dose is greater than or equal to $\delta_{thres,lm}$ cause the $m^{th}$ dose volume constraint for the organ to be violated.

b.  Advantages of this objective function include:

i. Well-understood quadratic
   ii. Function value is directly related to the dose of the target and critical organs; valuable for the user
   iii. User can drive optimization by changing the vectors associated with the dose volume constraint, w, d, v.
   iv. It is intuitive, i.e. a decrease in the objective function is directly related to an improvement in the dose distribution.

c.  Alternative Fitness/Objective/Cost functions may be employed.

i. Terms to include total treatment time optimization.
   ii. Terms to reduce the complexity of the solution, e.g. penalize large number of beams.

FIG. 6B

Heuristic Approximation a. The user selects dose volume constraints for the Fitness/Objective/Cost function.

b. Evolutionary Computing is described below, but other population based Heuristics may be employed such as Ant Colony and Particle-Swarm or a hybrid of multiple heuristics.

c. Generate an initial population of solutions subject to the following if applicable:
   i. Boundedness constraints
   ii. Sufficient diversity in the solutions.

d. Subsequent to generating the initial population of solutions, the Heuristic Algorithm evolves the population towards a global optimum through processes described, but not limited to: parent selection, cross-over, mutation, and survival selection. The algorithm processes may operate in series or parallel.
   i. Parent Selection chooses solution candidates to pass on traits to offspring.
   ii. Cross-Over determines how parent solutions are combined to create offspring solutions.
   iii. Mutation produces random changes.
   iv. Survival Selection determines which solutions in the current generation survive into the next generation.
   v. Local Particle Swarm Optimization refines a proper or improper subset of individuals.
   vi. Baldwinian and Lamarkian learning procedures allow for the propogation of learned improvements.

e. Dose-Volume Histograms (DVH) are updated after each generation to provide feedback to the user in real-time.

f. At the conclusion of the Heuristic Optimization, the most fit individual is selected from the population.

FIG. 7A

Genotype - Phenotype Mapping: Dose Calculation 0 50 48 1250 1000 923... 2

Dose Deposition Coefficients

Population

- An individual, $x_i$, is a single candidate solution.
  - $(N+1)$-tuple of numbers.

$$x_i = (0,0,1523.6,50.2,\ldots,0)$$

- A population, $P$, is a set of candidate solutions.
  - Denote size of population by m.

Scattered Crossover Operator

- Global population operator.
- Combines features of feasible solutions already visited in order to provide new potential candidate solutions with improved fitness function value.
- Explores the space between solutions.
- Randomly select values from each parent to pass on to offspring.

Lamarckian Beam Efficiency Meme

- Select an individual from the population.
- Find the gene with the smallest MU value.
- Set the MU value to zero.
- Redistribute the MU throughout the other genes.
- Compute the fitness of the new individual.
- Retain the new individual, if it is more fit than the original, otherwise retain the original.

$$x_i = (1523.5, 985, 64.1, \ldots, 43.9, 2)$$

$$x_j = (1523.1, 0, 985.1, 64.2, \ldots, 44.0, 2)$$

$$x_{retain} = arg(min(F(x_i), F(x_j)))$$

FIG. 7F

Local Particle Swarm Optimization Meme $$v_i \leftarrow \omega_i v_i + U_i(0, \varphi_1) \times (p_i - x_i) + U_i(0, \varphi_2) \times (p_g - x_i)$$
$$x_i \leftarrow x_i + v_i$$

- Choose a subset of individuals from the population.
- Apply canonical swarm intelligence algorithm in a local neighborhood.
- Retain the best individual solution at the conclusion of the swarm.
  - Improved fitness via local learning.

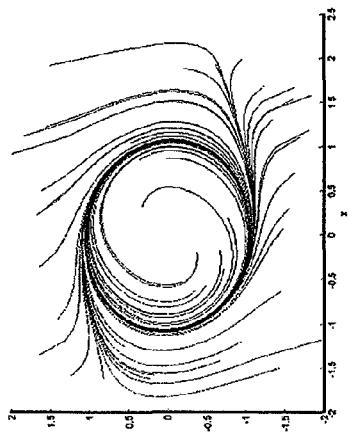

FIG. 7H

Truncation a. An optional step to reduce the solution search space for reasons including, but not limited to, those listed below:
        i. Decrease the number of beams.
        ii. Constrain the Beam Weight.
        iii. Increase the efficiency of local search.

b. Provides clinically deliverable plans given a modality's treatment delivery constraints.

FIG. 8

Local Search a. An optional step to fine-tune the output of the Heuristic Approximation.
    b. The local search may be performed on a single solution candidate or on multiple solution candidates. The local search can be stochastic or deterministic. One method is Sequential Quadratic Programming:
        i. User defines the dose volume constraints for target and critical organs.
        ii. Given a starting point, $x_0$, the point is passed to objective function.
        iii. At each iteration, the exact problem is approximated in a linear quadratic expansion. One term involves is an approximated Hessian updated using a Quasi-Newton method. The other term involves the gradient.

$$\min_{d \in \Re^n} \frac{1}{2} d^T H_k d + \nabla f(x_k)^T d$$

$$\nabla g_i(x_k)^T d + g_i(x_k) = 0, \quad i = 1, \ldots, m_e$$

$$\nabla g_i(x_k)^T d + g_i(x_k) \leq 0, \quad i = m_e + 1, \ldots, m.$$

iv. The solution is used to form a new iterate:

$$x_{k+1} = x_k + \alpha_k d_k.$$

v. The step size, $\alpha$, and direction, d, for each iterate can be produced by trust-region method and/or line-search active-set or interior point methods.
        vi. This continues until the optimization reaches a minimum or terminated by the user.

FIG. 9

Dosimetric Optimization

| VOI Name | Volume (%) | Dose (cGy) | Weight |
|---|---|---|---|
| PTV | 95 | 7600 | 1 |
| PTV | 0 | 8300 | 1 |
| BLADDER | 35 | 4000 | 0.2 |
| RECTUM | 25 | 4000 | 0.2 |
| INNER | 0 | 8100 | 0.4 |
| OUTER | 0 | 7100 | 0.4 |
| RING40 | 0 | 5000 | 0.4 |
| Skin | 0 | 3900 | |
| | | | |
| | | | |
| | | | |

Upper # of Beams: 100
Population Size: 10000
Mutation Rate: 80000
Crossover Fraction: 0.95
Elite Count: 1
Tournament Size: 10
Min MU: 200
Max MU: 1500
Min Skip: 100
Max Skip: 100
Truncation Cutoff: 0
Finetune x0:

☑ Heuristic Output
☐ Last SQP Output

Heuristic Optimization
Truncate
Finetune Optimization
Reset Population

FIG. 10

SYSTEM AND METHOD FOR RADIATION THERAPY TREATMENT PLANNING USING A MEMETIC OPTIMIZATION ALGORITHM

CROSS-REFERENCE TO RELATED APPLICATIONS

The present application claims the benefit of and priority to U.S. Provisional Application Ser. No. 61/165,051, filed on Mar. 31, 2009, entitled "METHOD FOR RADIATION THERAPY TREATMENT PLANNING USING A MEMETIC OPTIMIZATION ALGORITHM" to Owen Clark Clancy and Matthew Roy Witten, and to U.S. Provisional Application Ser. No. 61/306,243, filed on Feb. 19, 2010, entitled "SYSTEM AND METHOD FOR RADIATION THERAPY TREATMENT PLANNING USING A MEMETIC OPTIMIZATION ALGORITHM" to Owen Clark Clancy and Matthew Roy Witten; the entire contents of both are hereby incorporated by reference in their entirety for all purposes

BACKGROUND

1. Technical Field

The present disclosure relates to the field of radiation therapy treatment planning, and, more particularly, to a system and a computer-implemented method for beam weight optimization that includes population-based heuristics, population-based meta-heuristics, memes, local search, and/or local or global learning procedures.

2. Description of Related Art

Radiotherapy is a technique of treating tumors within a patient using beams of ionizing radiation. An objective in a radiotherapy procedure is to deliver a desired dose of radiation to a targeted tumor volume while limiting the amount of radiation received by surrounding tissue. This is accomplished by directing a series of radiation beams into a patient from different directions whereby the locus of the series of beams coincides with the tumor volume. While the surrounding tissue along the path of a beam may receive only a small fraction of the radiation dose, the tumor located at the intersection of the series of beams receives a much greater aggregate radiation dose.

The properties of the series of beams, e.g., the number, angle, intensity, aperture, and duration thereof is referred to in the art as a treatment plan. One objective of a treatment plan is to minimize the amount of radiation received by vital organs which may be located near the target tumor while delivering a prescribed radiation dose to the tumor. Such organs may be referred to as organs at risk (OAR). When preparing a treatment plan it must also be considered which, if any, of the surrounding organs have an increased sensitivity to radiation damage when compared to other organs in the treatment field. Surgical implants, such as and without limitation, internal bone fixations or cardiac pacemakers, may also be considered. Thus, another objective of a treatment plan is to ensure the amount of radiation received by particularly radiosensitive organs adjacent to the targeted tumor is limited to a dose lower than that where damage or undesirable side effects may occur.

Treatment planning methodologies fall broadly within two recognized types: forward planning, and inverse planning. Forward planning is a generally manual process whereby the practitioner empirically determines the treatment plan based on the dose to be delivered to the tumor, and thereafter identifies as a side-effect the collateral dose imposed on surrounding tissue and organs. Inverse planning is a computer-executed process whereby a practitioner specifies dose-volume constraints as input to an inverse planning algorithm, which is then executed on a processor to develop a treatment plan. Dose-volume constraints may include a target volume, minimum and maximum doses to be delivered to the target to achieve a therapeutic objective, and dose-volume limits to be delivered to surrounding tissues and organs. During inverse planning, non-targeted organs and/or tissue may be assigned a weighting factor related to the sensitivity of the non-targeted organs and/or tissue to radiation, which is taken into account while arriving at a suitable treatment plan.

The quality of a treatment plan may be assessed in part by its dose homogeneity, which is defined as the uniformity of radiation dose throughout the targeted tumor volume, and by its conformality, which is defined as the degree to which the delivered radiation dose conforms to the size and shape of the target tumor, e.g., the planning treatment volume, or PTV. Known inverse planning algorithms may be computationally intensive, and even using current processors such as an Intel® Core™ 2 Duo Processor, a treatment plan may take hours to develop.

In standard radiotherapy treatment delivery, a radiation source is mounted on a gantry capable of rotation in a single plane about a fixed point of rotation known as the isocenter. In a type of radiotherapy known as Intensity Modulated Radiation Therapy (IMRT), a "step and shoot" or "sliding window" approach is employed wherein the radiation source is placed in a fixed position in accordance with the treatment plan, the beam is activated for a prescribed duration and then deactivated, and the radiation source is repositioned while deactivated as it is being repositioned for the next beam. In another type of radiotherapy known as Intensity Modulated Arc Therapy (IMAT), a "moving beam" paradigm is employed wherein during an activation period the beam is moved through an arc centered around the tumor volume.

In robotic radiotherapy, a radiation source is mounted on a robotic arm. The radiation source and robotic arm are controlled by a computer programmed to position and activate the radiation source within a range of angles and intensities during treatment in accordance with a predetermined treatment plan.

A treatment planning method that provides improved homogeneity and conformality, reduced exposure of surrounding tissue to undesirable radiation, with reduced computational requirements would be a welcomed advance.

SUMMARY

In one embodiment of the present disclosure, a method of radiotherapy treatment planning is provided. The method includes: determining a set of beam geometry and dosimetric parameters from a totality of beams; calculating dose deposition coefficients responsive to the beam geometry and dosimetric parameters; and generating a set of points corresponding to a tissue volume. Each point corresponds to a place of interaction of a beam with a tissue volume. The method further includes identifying a solution subset of beams from the totality of beams; evaluating the solution based on at least one of an objective, fitness, or cost function; and activating a radiation source in accordance with the solution.

The objective function may comprise a quadratic function of the form shown in Equation 1 as follows:

$$F_{fit}(\vec{x}, \vec{w}, \vec{d}, \vec{v}) = \Theta(v_{t,min} - v_{p,min})w_{t,min} \sum_{1}^{n_t} \Theta\left(\delta_{thres,min} - \sum_{1}^{b} DDC_{ij}x_j\right)\left(\sum_{1}^{b} DDC_{ij}x_j - d_{p,min}\right)^2 + \Theta(v_{t,max} - v_{p,max})w_{t,max} \sum_{1}^{n_t} \Theta\left(\sum_{1}^{b} DDC_{ij}x_j - \delta_{thres,max}\right)\left(\sum_{1}^{b} DDC_{ij}x_j - d_{p,max}\right)^2 + \sum_{l=1}^{org}\left[\sum_{m=1}^{c_{lm}}[\Theta(v_{lm} - v_{p,lm})]w_{lm} \sum_{1}^{n_l} \Theta\left(\sum_{1}^{b} DDC_{kj}x_j - \delta_{thres,lm}\right)\left(\sum_{1}^{b} DDC_{kj}x_j - d_{p,lm}\right)^2\right].$$ (1)

The identifying step may be performed in accordance with at least one of population-based heuristics, population-based meta-heuristics, memes, a local search, local global learning procedures, or global learning procedures. In other embodiments, the identifying step may be performed in accordance with a population-based meta-heuristic global optimization including at least one of evolutionary computation, ant colony, and swarm intelligence, neural networks, differential evolution, artificial life, cultural algorithms, harmony search, artificial immune systems, learnable evolution models, and tabu search.

In another embodiment of the present disclosure, a method of radiotherapy treatment planning may include: selecting at least one parent candidate; combining parent candidates to generate at least one offspring solution; generating at least one random mutation solution; applying a local or global learning procedure to at least one individual solution; and selecting at least one survival candidate from at least one of an offspring solution, a mutation solution, or a learning procedure solution. Additionally or alternatively, the method may include performing a local search in the solution subset utilizing at least one of conjugate gradient, a gradient method and linear programming.

In yet another embodiment of the present disclosure, a radiotherapy system includes a planning apparatus and a radiation treatment apparatus. The planning apparatus includes one or more processors and a computer-readable storage medium. The computer-readable storage medium is in communication with the one or more processors and includes one or more programming instructions for: determining a set of beam geometry and dosimetric parameters from a totality of beams; calculating dose deposition coefficients responsive to the beam geometry and dosimetric parameters; and generating a set of points corresponding to a tissue volume. Each of the points corresponds to a place of interaction of a beam with a tissue volume. The one or more programming instructions may also include instructions for identifying a solution subset of beams from the totality of beams and evaluating the solution subset based on an objective function. The radiation treatment apparatus receives the evaluated solution subset and applies radiation to a planning treatment volume in accordance with the evaluated solution subset. The objective function may be equation 1 as shown supra.

The one or more programming instructions for identifying may be performed in accordance with at least one of population-based heuristics, population-based meta-heuristics, memes, local search, local global learning procedures, and/or global learning procedures. In some embodiments, the one or more programming instructions for identifying are performed in accordance with a population-based meta-heuristic global optimization including one or more of an evolutionary computation, ant colony, and swarm intelligence, neural networks, differential evolution, artificial life, cultural algorithms, harmony search, artificial immune systems, learnable evolution models, and tabu search.

In yet another embodiment, the one or more one or more programming instructions further includes selecting at least one parent candidate; combining parent candidates to generate at least one offspring solution; generating at least one random mutation solution; applying a local or global learning procedure to at least one individual solution; and selecting at least one survival candidate from one or more of an offspring solution, a mutation solution, and/or a learning procedure solution. Additionally, the one or more programming instructions may further include performing a local search in the solution subset.

In another embodiment of the present disclosure, a radiotherapy planning system includes at least one processor and machine-readable media. The machine-readable media comprises a set of executable instructions adapted for execution on the one or more processors. The set of executable instructions for performing radiotherapy planning including: receiving a first dose-volume constraint for a planning treatment volume; receiving a second dose-volume constraint for tissue outside of said planning treatment volume; determining a set of beam properties for a plurality of beams using a population-based heuristic approximation in accordance with the first and second dose-volume constraints; refining the set of beam properties for the plurality of beams using a deterministic local trajectory search; and generating a set of instructions to instruct a radiation treatment apparatus to apply radiation to the planning treatment volume in accordance with the plurality of beams having the refined set of beam properties. The set of executable instructions may include instructions for evaluating a beam property of the set of beam properties for a beam of the plurality of beams using Equation 1 shown supra. The population-based heuristic approximation may be a population-based meta-heuristic global optimization. The population-based meta-heuristic global optimization may include one or more of evolutionary computation, ant colony, and swarm intelligence, neural networks, differential evolution, artificial life, cultural algorithms, harmony search, artificial immune systems, learnable evolution models, and tabu search.

In yet another embodiment of the present disclosure, a radiotherapy treatment planning system is disclosed and includes a processor means, a storage means, a parameterization means, a geometric point representation means, an evaluation means, and a heuristic means. The processor means (e.g., one or more of: a processor, a FPGA, a PAL, a PLD, a CPLD, an ASIC, a SoC, and the like) executes a set of instructions for radiation treatment planning. The storage means (e.g., one or more of: a hard disk, magnetic storage, a magnetic disk, volatile memory, non-volatile memory, flash memory, an EEPROM, solid-state storage, optical storage, a magneto-optical disc storage, RAM, ROM, dynamic memory, static memory, firmware storage, and the like) stores the set of instructions. The parameterization means, the geometric point representation means, the evaluation means, and the heuristic means are executable on the processor means and storable on the storage means. The parameterization means determines geometry and dosimetric parameters for a radiation beam directed to a treatment tissue volume. The geometric point representation means selects a point of the treatment tissue volume. The evaluation means evaluates the geometry and dosimetric parameters directed to the point of the treatment tissue volume. The heuristic means heuristically determines a treatment plan in accordance with the evaluation of the geometry and dosimetrics parameters.

The treatment planning system may also include a truncation means, a local search means, and/or a radiation means. The truncation means and the local search means are executable on the processor means and storable on the storage means. The truncation means truncates a beam of the treatment plan. The local search means optimizes a beam of the treatment plan. The radiation means irradiates the treatment tissue volume in accordance with the treatment plan. The radiation means includes the following radiation apparatuses for irradiating the treatment tissue volume in accordance with the treatment plan: a radiation source mounted on a gantry, an Intensity Modulated Radiation Therapy apparatus, an Intensity Modulated Arc Therapy apparatus, a radiation source mounted on a robotic arm, a frameless robotic radiosurgery apparatus, and the like.

In yet another embodiment of the present disclosure, a radiotherapy treatment planning system includes a set of executable instructions for performing radiotherapy planning including: generating a population of individuals; and evaluating each individual of the population by sampling a first set of points. Each of the first set of points corresponds to tissue. The set of executable instructions further includes evaluating each individual of the population by sampling a second set of points. Each of the second set of points corresponds to tissue. The second set of points is different from the first set of points.

In yet another embodiment of the present disclosure, a radiation treatment apparatus includes a radiation source, a positioning apparatus and a control system. The radiation source is adapted to emit radiation in response to an activate command. The positioning apparatus positions the radiation source. The control system is in operative communication with the positioning apparatus and positions the radiation source. The control system issues the activate command to the radiation source. The control system positions the positioning apparatus and issues the activate command for a memetically determined amount of time.

These and other features, aspects, and advantages of the present disclosure will become better understood with reference to the following description and appended claims.

BRIEF DESCRIPTION OF THE DRAWINGS

The above and other aspects, features, and advantages of the present disclosure will become more apparent in light of the accompanying drawings attached hereto and in the embodiments presented herein, wherein:

FIG. 3 depicts a pseudocode overview of radiation treatment planning in accordance with the present disclosure;

FIGS. 4-5, 6A-6B, 7A-J, 8 and 9 show in more detail the pseudocode overview as shown in FIG. 3 in accordance with the present disclosure;

FIG. 10. depicts an embodiment of a user interface of a radiation therapy treatment planning system in accordance with the present disclosure;

DETAILED DESCRIPTION

As used herein, the term "beam weight" may refer to an individual beam weight in robotic radiosurgery, to an individual bixel weight in IMRT, to an individual arc segment weight in VMAT, and/or to an individual 3DCRT beam weight; the term "weight" refers to monitor units (MU) or beam-on time.

The disclosed method of treatment planning includes the following aspects listed hereinbelow, which will be described in detail.

Figure 1:
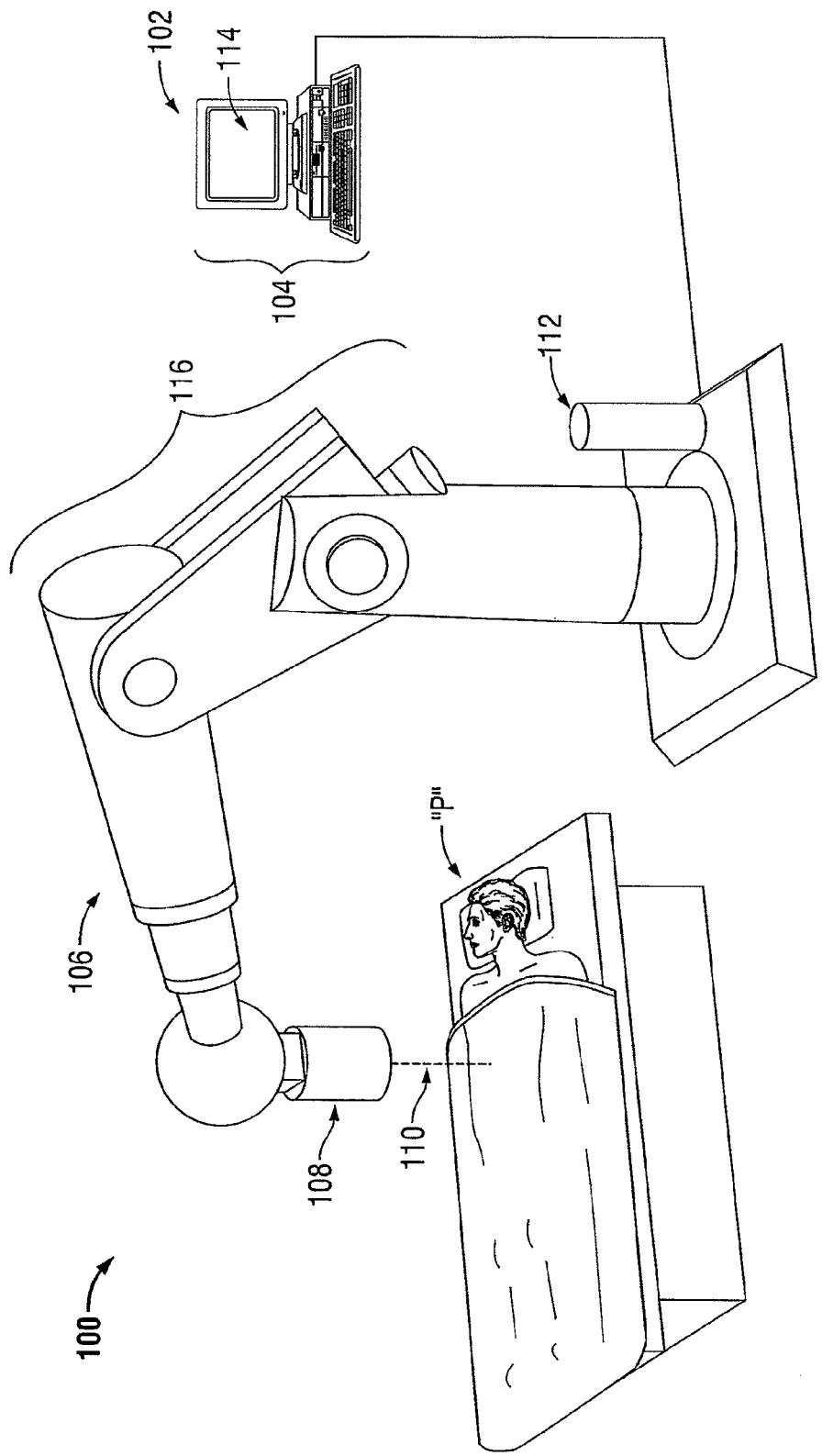
FIG. 1 shows a radiation treatment system including a planning apparatus and a radiation treatment apparatus in accordance with the present disclosure.

Referring to the drawings, FIG. 1 shows a radiation treatment system 100. System 100 includes a planning apparatus 102 having a planning terminal 104. System 100 also includes a radiation treatment apparatus 106 having a radiation source 108 adapted to direct radiation 110 towards treatment tissue volume of patient P. The treatment tissue volume is the targeted tissue, e.g., the targeted cancerous tumor. However, the treatment tissue volume may be surrounded by healthy tissue and/or organs.

A user utilizes the planning terminal 104 to generate a radiotherapy treatment plan to treat the patient P. The radiotherapy treatment plan preferably achieves target radiation doses for the treatment tissue volume while minimizing the radiation dose of non-targeted tissue. For example, an effective radiotherapy treatment plan targeting cancerous tissue exposes the cancerous tissue with radiation doses sufficient to cause cell death while minimizing the radiation exposure of healthy tissue and organs. Different tissue types and organs have varying degrees of radiation sensitivity.

The user utilizes the planning terminal 104 to generate a treatment plan. The planning terminal 104 communicates the treatment plan to the radiation treatment apparatus 106 e.g., via a network, a data cable, a floppy disk, a thumbdrive, the internet, or other communications technology. The radiation treatment apparatus 106 applies radiation 110 to patient P in accordance with the treatment plan.

The radiation treatment apparatus 106 includes a control system 112 that instructs the radiation treatment apparatus 106 to position the radiation source 108 to apply the radiation 110 to patient P. The control system 112 can also issue an activate command to the radiation source 108 to activate the generation of the radiation 110. The radiation treatment apparatus 106 includes multiple axes of rotation to position the radiation source 108 in 3-dimensional space to direct the radiation 110 towards the treatment tissue volume while minimizing the radiation exposure of healthy tissue and organs. The positioning apparatus 116 positions the radiation source 108. The positioning apparatus 116 is shown as a robotic arm. In various embodiments, the positioning apparatus may be a gantry, a robotic arm, a frameless robotic radiosurgery positioning apparatus, and the like. Various parameters are accounted for to facilitate effective clinical outcomes. For example, the treatment plan is optimized to achieve sufficient dose homogeneity and conformality. The treatment plan includes instructions for applying the radiation 110 to the tissue treatment volume; the instructions may include target properties of a series of beams, e.g., the number, angle, intensity, aperture, and duration thereof.

The disclosed radiation treatment planning method, e.g., the planning apparatus 102 can generate a treatment plan, may be embodied in software, hardware, firmware, microcode, a virtual machine, software in execution, bytecode, in simulation, on a personal computer (e.g., planning terminal 104), and the like. For example, planning apparatus 102 may include a personal computer (e.g., planning terminal 104) having specialized hardware (not explicitly shown), and may implement all or a portion of a radiation treatment planning method in a VHDL programmed FPGA. The planning apparatus 102 may encompass one or more processors configured to execute a set of instructions for executing a radiation treatment planning method disclosed herein. In some embodiments, the disclosed radiation treatment planning may be embodied in one or more software modules (discussed below). The one or more processors may be operatively coupled to the radiation treatment apparatus 106 which is adapted to deliver radiation therapy to the patient P. The radiation treatment apparatus 106 may be, but is not limited to, a standard radiotherapy treatment delivery apparatus, an IMRT radiotherapy treatment delivery apparatus, and/or an IMAT apparatus.

Figure 2:
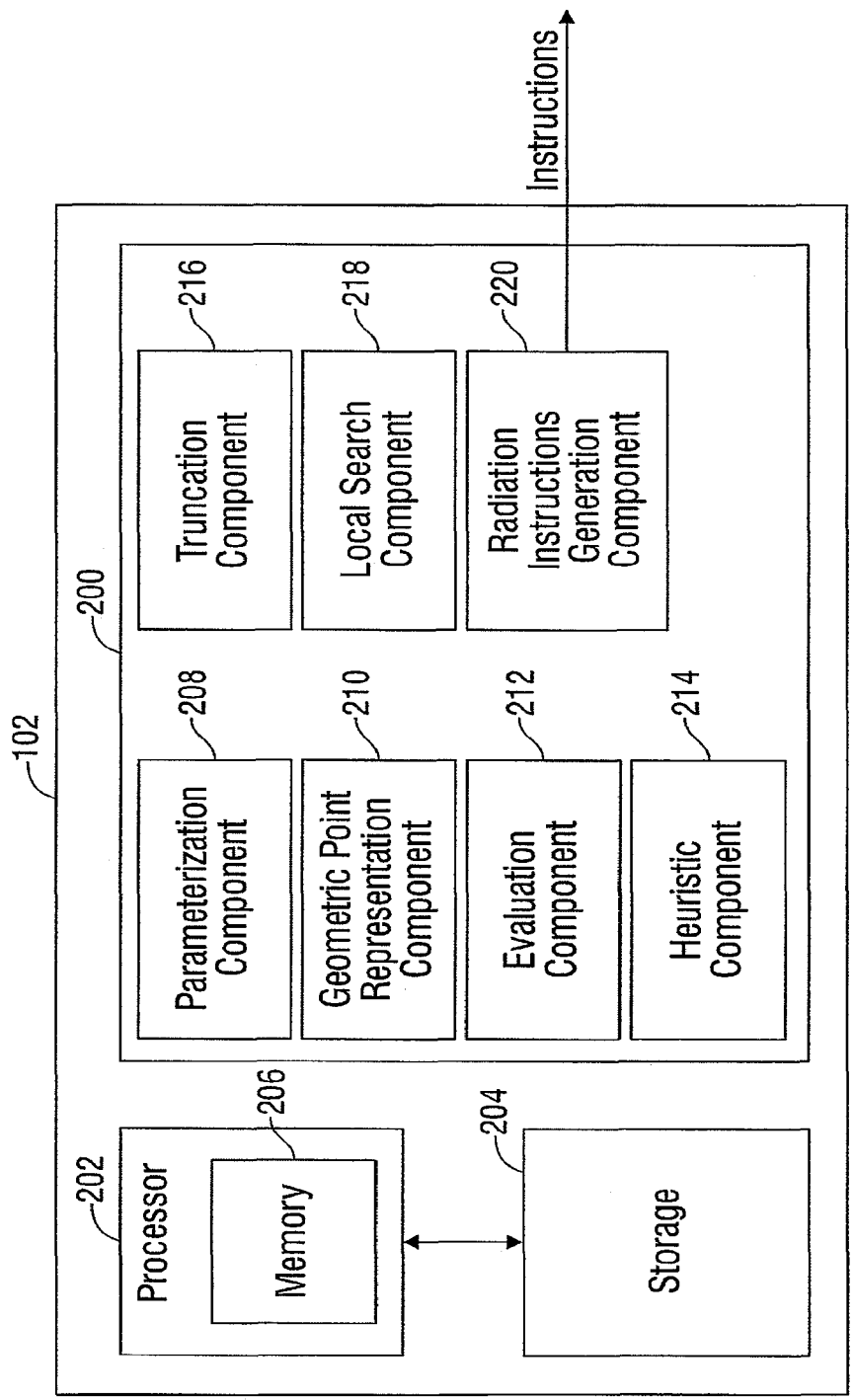
FIG. 2 depicts a block diagram of an embodiment of the planning apparatus of FIG. 1 in accordance with the present disclosure.

Referring to the drawings, FIG. 2 is a block diagram of a planning apparatus 102' that is an embodiment of the planning apparatus 102 of FIG. 1. The planning apparatus 102' includes a radiotherapy planning component 200, a processor 202, and a storage 204. The storage 204 may be a hard disk, magnetic storage, a magnetic disk, volatile memory, non-volatile memory, flash memory, an EEPROM, solid-state storage, optical storage, a magneto-optical disc storage, RAM, ROM, dynamic memory, static memory, firmware storage, and the like. The processor 202 includes a memory 206. Memory 206 is readily accessible by processor 202. The radiotherapy planning component 200 may be implemented as software adapted for execution on the processor 202. The radiotherapy planning component 200 may also be stored in storage 204 for retrieval by processor 202 when requested by processor 202. The radiotherapy planning component 200 includes a parameterization component 208, a geometric point representation component 210, an evaluation component 212, a heuristics component 214, a truncations component 216, a local search component 218, and a radiation instructions generation component 220. The radiotherapy planning component 200 can generate radiation treatment instructions for the radiation treatment apparatus 106 of FIG. 1.

A user using planning apparatus 102' can specify dose-volume constraints, wherein it is possible to specify, for each tissue volume (e.g., OAR), a maximum OAR volume which may receive a predetermined dose. For way of example, and without limitation, a practitioner may dictate that for each surrounding organ, no more than 5% of each organ receives a predetermined dose. The practitioner may also specify dose-volume constraints for one or more targets. For example, and without limitation, a practitioner may specify that at least 95% of the PTV must receive the full prescription dose and 0% may receive 120% of the prescription dose.

The radiotherapy planning component 200 allows for the representation of the target or targets, and the OARs, to be dynamic (e.g., not fixed.) The process of dynamic point sampling, wherein the number of points allocated to a particular volume changes throughout the optimization, according to a prescribed functional dependence, provides a method of altering the number of optimization points in a given volume of interest as the optimization progresses.

The radiotherapy planning component 200 allows for a dynamic reduction in the dimension of the search space with each iteration, up to the point where the beam weight set achieves maximal efficiency, e.g., as the optimization proceeds, dimensions associated with inefficient beams are removed from the search space through Baldwinian and Lamarckian memes. The process of progressively reducing the dimensionality of the search space improves the run-time performance of the algorithm.

The radiotherapy planning component 200 provides a dose-volume histogram (DVH) which may be updated in real-time during execution of iterative treatment planning steps. In another aspect, an iterative process may be suspended, permitting the practitioner to specify alternative or modified dose-volume constraints.

The radiotherapy planning component 200 provides a dosimetric objective, or fitness, function which seeks to optimize a treatment plan in accordance with dose-volume constraints, e.g., wherein the deviations in doses to points within the tumor volume from the dose-volume constraints and/or to points within the surrounding OARs from the dose-volume constraints are minimized.

The radiotherapy planning component 200 generates an initial population of solutions, subject to boundedness constraints (e.g., maximum and minimum allowable monitor unit settings) and having sufficient diversity in the initial solution set. A heuristic optimization algorithm of heuristic component 214 evolves the population towards a global optimum through, for example and without limitation, parent selection, cross-over, mutation, survival selection, local particle swarm optimization (PSO), Baldwinian and Lamarckian learning procedures, or memes. The algorithm processes may execute in series or parallel. In more detail, parent selection chooses solution candidates to pass on traits to offspring solutions. Cross-over determines how parent solutions are combined to create offspring solutions. Mutation produces random changes in the solutions. Survival selection determines which solutions in the current generation survive into the next generation (e.g., next iteration.) Local particle swarm optimization improves the fitness of a proper or improper subset of the population of individuals. Baldwinian and Lamarckian learning propagate learned improvements. Upon conclusion of the heuristic optimization algorithm, an approximation to the solution at which the global minimum of the objective function is obtained is identified.

Radiotherapy planning component 200 may also allow for the coevolution of memes as the optimization proceeds.

Additionally or alternatively, a local search optimization may be performed by local search component 218 to fine-tune the output of the heuristic approximation. The local search may be performed on a single solution candidate or on multiple solution candidates. The local search can be stochastic or deterministic.

Aspects of a memetic optimization method for radiosurgery treatment in accordance with the present disclosure is illustrated herein with reference to the following pseudocode and written description.

FIG. 3 shows pseudocode 300 which is an overview of the radiotherapy planning component 200. The pseudocode code 300 includes lines 1 through 20. Line 1 initializes the variables and generates the initial problem specific population. An individual is a radiation treatment plan that may be used. That is, an individual is a hypothetical radiation treatment that may or may not be used to treat a patient. A population of individuals is a subset of the solution space of possible treatment plans. Each individual is preferably constrained to a target hardware configuration, e.g., the radiation treatment apparatus 106. In some embodiments, each individual can include as many beams as the hardware allows, e.g., the radiation treatment apparatus 106 has a finite number of locations that radiation source 108 may be located and a finite number of directions that the radiation 110 may be directed towards for each position. However, most treatment plans represent a subset of the possible positions and orientations of the target hardware, e.g., the radiation source 108. Each chosen position and orientation is associated with a beam weight. The beam weights are also part of each individual and are beam and individual specific.

As previously mentioned, line 1 does not necessary generate the initial population of individuals where each individual has all possible beams possible by the hardware constraints of the radiation treatment apparatus 106 of FIG. 1. A limited number of beams may be contained in each individual during generation of the initial problem-specific population of line 1 that is less than all possible beams of radiation treatment apparatus 106. Lines 2-15 evolve the population and each individual of the population may be subject to changes based upon predetermined criteria. The best individual is selected for local refinement via lines 16-20. Individual fitness is evaluated by an objective function, e.g., Equation 1 above.

Lines 3-15 form a while loop. The while loop refines the population until a terminal condition is satisfied as indicated by line 3. A terminal condition may include, but is not limited to, a user interruption, the fittest individual of the population does not improve beyond a predefined threshold per unit time, a predetermined fitness is reached, and the like. Line 4 applies problem-specific operators such as deleting individuals satisfying predetermined criteria, such predetermined criteria may include high correlation between individuals, uniformity among fitness values, fitness values themselves, random selection, and the like, and, in a parallel process, may determine the number of points representing the volume of tissue in software via dynamic point sampling of the optimization points. Line 5 applies cultural memes such as beam reduction; wherein a given beam which has identically zero monitor unit values for all individuals in the population is removed from the search space. Line 6 calculates the fitness scores of individuals using a cost function, e.g., the objective function as shown in Equation 1 supra. Line 7 allows the best individuals to survive to the next generation. Line 8 selects parents based upon fitness. Line 8 utilizes a survival of the fittest algorithm (in the evolutionary sense). Alternative algorithms for line 8 include, heuristic algorithms, such as heuristic operators, diversification operators, and intensification operators. Lines 9-11 perform a local search. Line 9 may select a fraction of individuals from the population. Line 10 utilizes local memes to act on the individuals. The local search of line 11 uses Lamarckian learning to create offspring, e.g., using heuristic operators, local cross-over memes, iterative improvement memes, local beam efficiency memes, local particle swarm operators, ant colony, and/or swarm intelligence.

Lines 12-14 perform global improvements. Line 12, for example, applies population operators to create offspring, e.g., using heuristic operators, cross-over, particle swarm operators, ant colony, and/or swarm intelligence. There may be no offspring selection pressure as shown in line 14. Line 15 defines the end of the while loop of lines 2-15. Lines 16-19 locally refine the best individual. That is, the best individual of the entire population is chosen to proceed to lines 16-19. The best individual is determined by applying a fitness function to individuals of the population, e.g., using the objective function as shown in Equation 1 supra. Lines 17 through 19 form a while loop which continues until a termination condition terminates the while loop, such as the fittest individual does not improve beyond a predefined threshold per unit time, a predetermined fitness is reached, or the user manually terminates the optimization. Line 18 applies a conjugate gradient algorithm to refine the best individual. Alternatives for the conjugate gradient algorithm may be, without limitation, for example simulated annealing, linear programming, branch and bound, and the like.

Referring again to FIG. 2, and as previously mentioned, the radiotherapy planning component 200 includes the parameterization component 208, the geometric point representation component 210, the evaluation component 212, the heuristics component 214, the truncations component 216, the local search component 218, and the radiation instructions generation component 220. The radiotherapy planning component 200 can generate radiation treatment instructions for the radiation treatment apparatus 106 of FIG. 1.

The parameterization component 208 is outlined in pseudocode in FIG. 4. The geometric point representation component 210 is outlined in pseudocode in FIG. 5. The evaluation component 212 is outlined in pseudocode in FIGS. 6A-6B. The heuristic component 214 is outlined in pseudocode in FIG. 7. The truncation component 216 is outlined in pseudocode in FIG. 8. The local search component 218 is outlined in pseudocode in FIG. 9. After an individual is refined (e.g., after line 20 of FIG. 3) radiation instructions generation component 220 generates instructions for radiation treatment apparatus 106.

FIG. 4 shows an outline in pseudocode of the parameterization component 208 of FIG. 2. The parameterization component 208 can generate dosimetric parameters for a population utilizing the totality of beams consists of all possible beams given the hardware constraints of the modality. For the totality of beams, the parameterization component 208 calculates the following geometry for each beam using a ray-tracing algorithm along the beam's geometrical central axis: (1) Source to Axis Distance (SAD), the Euclidian distance from the origin of the radiation to the point of calculation, (2) Depth—distance from surface intersection point to the point of calculation, and (3) Off-Axis Distance (OAD)—distance in the plane perpendicular to the beam central axis to the point of calculation scaled back to a nominal SAD. The parameterization component 208 also calculates the dose at a given point by multiplying MU, the beam weight, by DCC (see below) to determine the dose received at a particular point by a particular beam. An aggregation of these calculations can be used to determine the total dose of radiation that will be received at a particular point of tissue when implementing the radiation therapy plan by using radiation treatment apparatus 106. The parameterization component 208 also calculates dose deposition coefficients from the beam geometry and the measured data for a particular treatment machine, e.g., radiation treatment apparatus 106. One method which may be utilized is the Khan method for dose calculation utilizing Equation 2, shown as follows:

$$DDC = OF \times \left(\frac{SAD}{F}\right)^2 \times TPR \times OCR. \quad (2)$$

DDC is the Dose Deposition Coefficient, OF is the Output Factor, TPR is the Tissue-Phantom Ratio, OCR is the Off-Center Ratio, and F is the Source-to-Calibration Point Distance. The parameterization component 208 calculates the dose per beam by multiplying the beam weight (MU) by DDC. Alternatively, a Monte Carlo or other model based dose calculation algorithms may be employed.

FIG. 5 shows an outline in pseudocode of the geometric point representation component 210 of FIG. 2. Points of tissue may be dynamically sampled when processing a population of individuals, e.g., points may be sampled for evaluating all individuals in a population and a different point set may be used for evaluating all of the individuals in a population after modifications are made to the individuals. The geometric point representation component 210 generates points on the boundary of the target or a critical organ from the contour set; additionally or alternatively, some points may be randomly generated inside the treatment tissue volume. The geometric point representation component 210 ensures that the representation of the target and the OARs by the points is not static throughout the optimization process, e.g., through lines 3-15. Using the process of dynamic point sampling, the number of points change according to a prescribed functional dependence, for example, the sampled points are chosen at line 4 and change during each iteration. The size of the set of sampled points increases before each iteration of the optimization processor. In other embodiments, the number of points may decrease. Possible functional dependences may be, for example and without limitation, exponential, linear, step-wise, and the like. The geometric point representation component 210 can ensure that as the number of iterations increases, the number of optimization points in a given volume of interest changes, e.g., increases or decreases by a predetermined amount.

FIGS. 6A-6B shows an outline in pseudocode of the evaluation component 212 of FIG. 2. The evaluation component 212 evaluates the fitness of an individual and provides a value describing its effectiveness in achieving the treatment planning goals. The evaluation component 212 can use the objective function shown in Equation 1 above. As also shown above, the objective function is shown in Equation 3 as follows:

$$F_{fit}(\vec{x}, \vec{w}, \vec{d}, \vec{v}) = \Theta(v_{t,min} - v_{p,min})w_{t,min} \quad (3)$$

$$\sum_{1}^{n_t} \Theta\left(\delta_{thres,min} - \sum_{1}^{b} DDC_{ij}x_j\right)\left(\sum_{1}^{b} DDC_{ij}x_j - d_{p,min}\right)^2 +$$

$$\Theta(v_{t,max} - v_{p,max})w_{t,max}$$

$$\sum_{1}^{n_t} \Theta\left(\sum_{1}^{b} DDC_{ij}x_j - \delta_{thres,max}\right)\left(\sum_{1}^{b} DDC_{ij}x_j - d_{p,max}\right)^2 +$$

$$\sum_{l=1}^{org}\left[\sum_{m=1}^{c_{lm}}[\Theta(v_{lm} - v_{p,lm})]w_{lm}\right.$$

-continued $$\left.\sum_{1}^{n_l}\Theta\left(\sum_{1}^{b}DDC_{kj}x_j - \delta_{thres,lm}\right)\left(\sum_{1}^{b}DDC_{kj}x_j - d_{p,lm}\right)^2\right].$$

Where: $F_{fit}$ is the Fitness/Objective/Cost function, x is a vector of beam weights (independent variables), w is a vector of constraint weights, d is a vector of doses associated with user selected dose volume constraints, v is a vector of volumes associated with user selected dose volume constraints, $\Theta$ is the Heaviside function defined to be zero when the argument is less than zero, otherwise one, subscript t refers to target, subscript p refers to target prescription dose, $n_t$ is the number of points calculated within the target, b is the number of beam weights, org is the number of critical organs, $c_{lm}$, is the $m^{th}$ constraints for the $1^{th}$ critical organ, $n_1$ is the number of points in the $1^{th}$ critical organ, $\delta_{thres,min}$ is the dose to that point in the target such that when all points in the target are sorted, points for which the dose is less than or equal to $\delta_{thres,min}$ cause the minimum dose volume constraint for the target to be violated, and $\delta_{thres,max}$ is the dose to that point in the target such that when all point in the target are sorted, points for which the dose is greater than or equal to $\delta_{thres,max}$ cause the maximum dose volume constraint for the target to be violated, and $\delta_{thres,lm}$ is the dose to that point in the $1^{th}$ critical organ such that when all points in the organ are sorted, points for which the dose is greater than or equal to $\delta_{thres,lm}$ cause the $m^{th}$ dose volume constraint for the organ to be violated.

Various advantages of the cost function shown in Equations 3 and 1 above, include: it is a understandable quadratic; the function value is directly related to the dose of the target and critical organs; it is valuable for the user of planning apparatus 102 of FIG. 1; a user of planning apparatus 102 can drive the optimization process by changing the vectors associated with the dose volume constraint (e.g., w, d, and/or v); and it is intuitive because a decrease in the results of the objective function is directly related to an improvement in the dose distribution. Other Alternative Fitness/Objective/Cost functions may be employed by evaluation component 212.

FIGS. 7A-7J show outlines in pseudocode of various aspects of the heuristic component 214 of FIG. 2. The heuristic component 214 allows a user of planning apparatus 102 to select dose volume constraints for the Fitness, Objective, and/or Cost function(s), e.g., the objective function of Equations 1 or 3. The heuristic component 214 may utilize various evolutionary computing techniques or algorithms, heuristics, ant colony, particle swarm, swarm intelligence or a hybrid. C through F of FIG. 7A describe a memetic computing implementation of the heuristic component 214. The heuristic component 214 can generate an initial population of solutions subject to (1) boundedness constraints, and (2) diversity requirements of the solution (i.e., there must be sufficient diversity in the solutions). Subsequent to generating the initial population of solutions, the heuristic algorithm of heuristic component 214 evolves the population towards a global optimum by utilizing various operators such as, but not limited to, parent selection, cross-over, mutation, and survival selection. Additionally or alternatively, various memes may be applied as part of the heuristic component, as shown in detail in FIGS. 7B-7J. The algorithm processes may operate in series or parallel.

The heuristic algorithm of heuristic component 214 may: (1) utilize a parent selection operator which chooses solution candidates to pass on traits to offspring; (2) utilize a cross-over operator which determines how parent solutions are combined to create offspring solutions; (3) utilize a mutation operator which produces random changes; (4) utilize a survival selection operator which determines which solutions in the current generation survive into the next generation; (5) utilize a local particle swarm optimization meme which refines a proper or improper subset of individuals; and (6) utilize Baldwinian and/or Lamarkian learning procedures which allow for the propagation of learned improvements. Additionally or alternatively, various memes may be applied as part of the heuristic component, as shown in detail in FIGS. 7B-7J. Five (5) and Six (6) may be implemented during local refinement such as shown in line 5, and lines 10 through 11 of the pseudocode of FIG. 3.

The heuristic component 214 also updates the Dose-Volume Histograms (DVH) after each generation to provide feedback to the user of the planning apparatus 102 of FIG. 1 (in some embodiments, real-time programming may be utilized). At the conclusion of the heuristic optimization iterations, the heuristic component 214 selects the most fit individual from the population for further refinement via lines 16-19 of the pseudocode of FIG. 3.

Figure 7B:
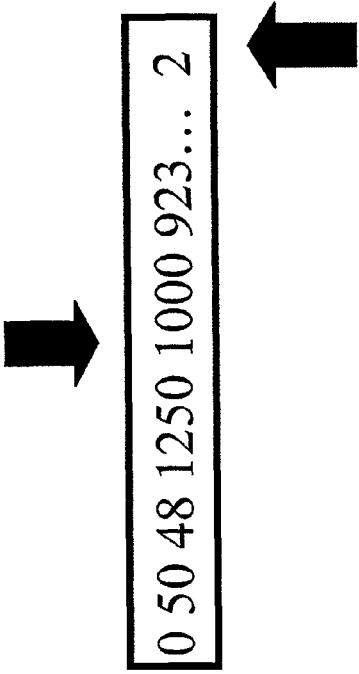
Figure 7C:
Figure 7E:
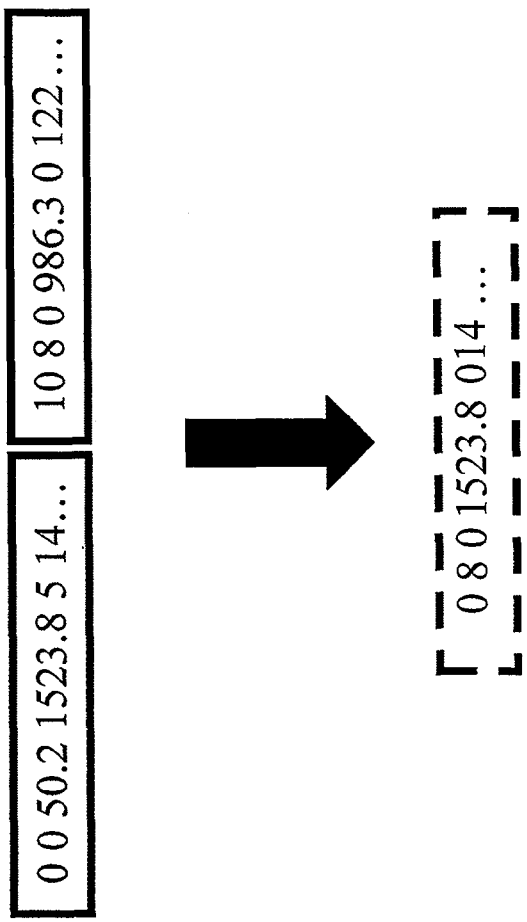

FIG. 7B illustrates the genotype space. The genotype space consist of an (N+1)-tuple of numbers. N is a positive real number for the beam weight values, MU, for each of N beams. A single integer value represents a meme. N is not a static value, but decreases during optimization as a result of beam reduction. FIG. 7C illustrates the genotype-phenotype mapping and the dose calculation. Dose Deposition Coefficients are calculated and map the genotype space of possible beam weight sets to the phenotype space of possible dose distributions. FIG. 7D illustrates the population of individuals. An individual, xi, is a single candidate solution and is a (N+1)-tuple of numbers. A population, P, is a set of candidate solutions. The size of the population is denoted by m. FIG. 7E illustrates the scattered crossover operator. The scattered crossover operator is a population operator. It combines features of feasible solutions already visited in order to provide new potential candidate solutions with an improved fitness function value. It explores the space between solutions. It also randomly selects values from each parent to pass on to offspring.

Figure 7G:
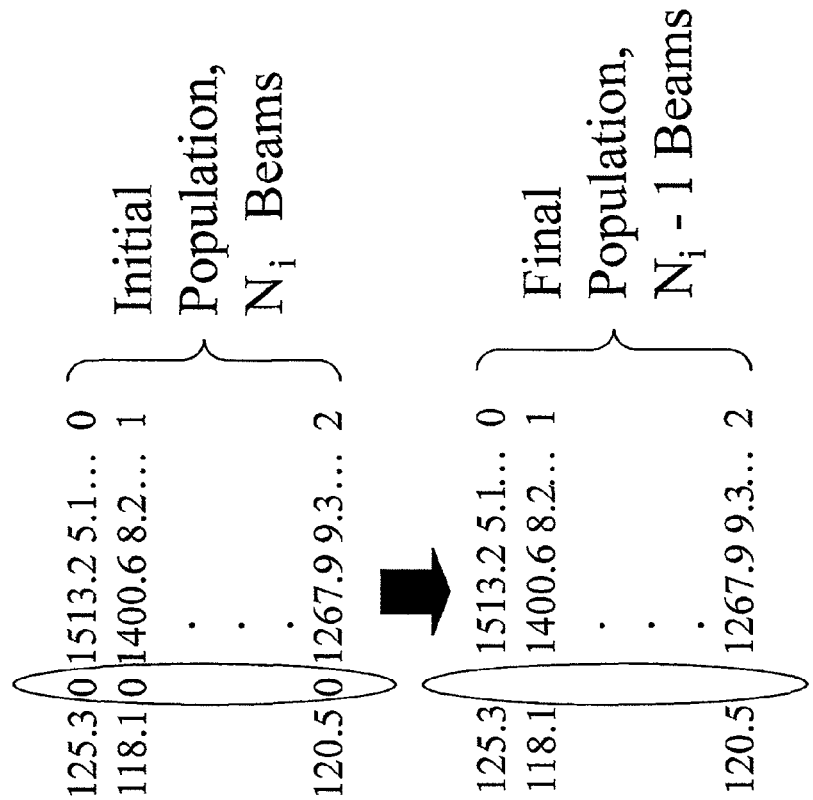
Figure 71:
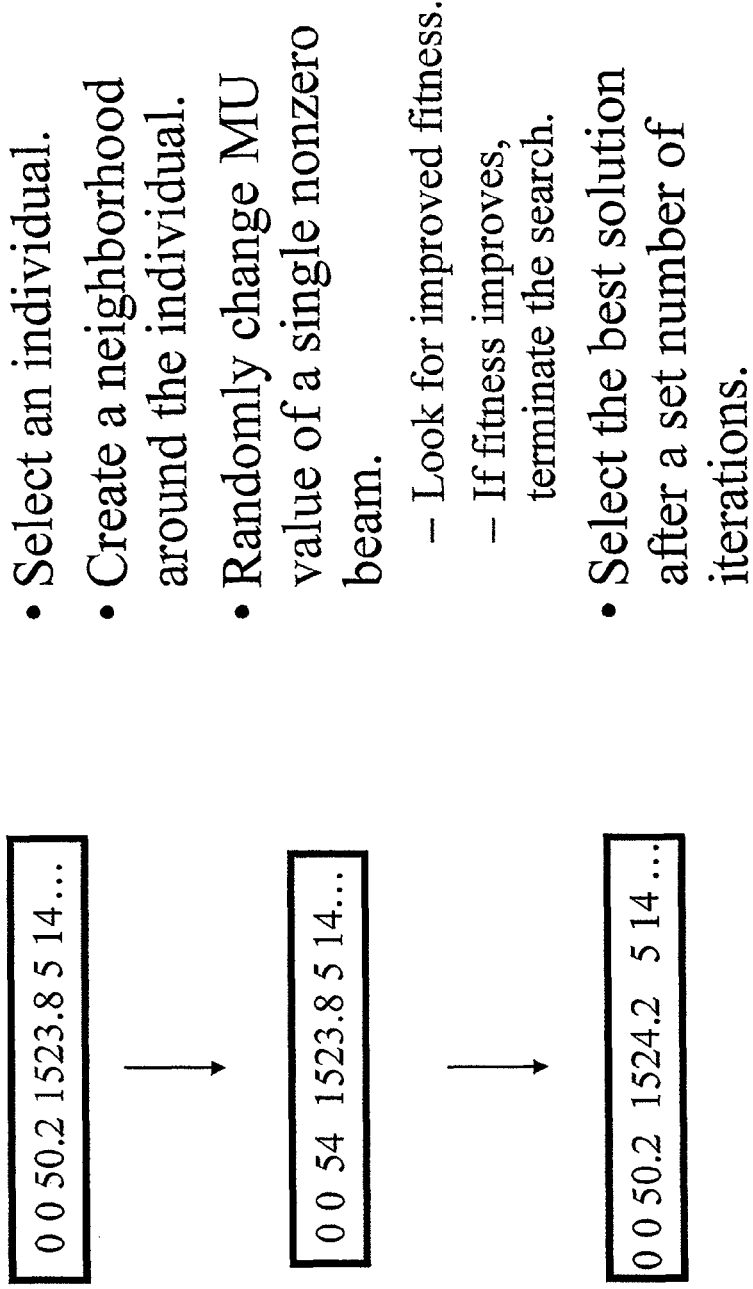

FIG. 7F illustrates the Lamarckian beam efficiency meme. The Lamarckian beam efficiency meme implements the following steps: select an individual from the population; find the gene with the smallest MU value; set the MU value to zero; redistribute the MU throughout the other genes; compute the fitness of the new individual; and retain the new individual, if it is more fit than the original, otherwise retain the original. FIG. 7G illustrates the Baldwinian beam reduction meme. The Baldwinian beam reduction meme implements the following steps: a cultural learning meme is applied to the population as a whole; a search is performed for a gene such that the MU value is zero for all individuals in the population; the gene is removed from the genome; the dimensionality of the search space is reduced (this improves the efficiency of the algorithm as a whole); and the number of beams from Ni to Ni-1 is reduced. Ni is the number of beams at the start of the ith iteration.

FIG. 7H illustrates a local particle swarm optimization meme. The local particle swarm optimization meme: chooses a subset of individuals from the population; applies a canonical swarm intelligence algorithm in a local neighborhood; and retains the best individual solution at the conclusion of the swarm. This improves the fitness of the individuals utilizing local learning.

Figure 7J:
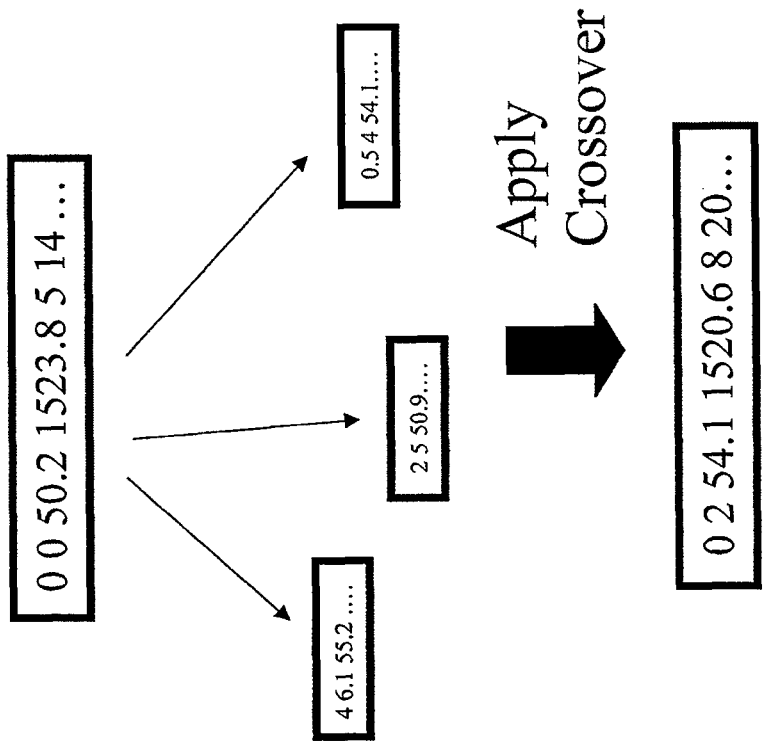

FIG. 7I illustrates an iterative improvement meme. The iterative improvement meme: selects an individual; creates a neighborhood around the individual; randomly changes a MU value of a single nonzero beam (this is to improve the fitness of an individual, if the fitness of the individual improves, termination of the search is preferable); and select the best solution after a set number of iterations. FIG. 7J illustrates the local crossover meme. The local crossover meme is similar to the global crossover meme and may utilize the same operator. The local crossover meme performs the following steps: select an individual and creates solutions around that individual to form a parent population; perform a crossover using the population; and search for an improvement in fitness.

FIG. 8 shows an outline in pseudocode of the truncation component 216 of FIG. 2. The truncation component 216 truncates between lines 15 and 16 of the pseudocode of FIG. 3. Truncation is an optional step to reduce the solution search space for various reasons, including: to decrease the number of beams, to constrain the beam weight and/or to increase the efficiency of local search. Truncation can provide clinically deliverable plans given a modality's treatment delivery constraints including: no non-negative beam weights, or limiting beams such that it is geometrically feasible to deliver radiation from a particular location.

FIG. 9 shows an outline in pseudocode of the local search component 218 of FIG. 2. The local search component 218 performs its algorithm in lines 16-19 of the pseudocode of FIG. 3. The local search component 218 is an optional step to fine tune the output of the heuristic component 214 of FIG. 2. In some embodiments, lines 16-19 of the pseudocode of FIG. 3 may process more than one candidate. The local search component 218 may perform a local search on a single solution candidate or on multiple solution candidates. The local search can be stochastic or deterministic. One way of performing a local search is a Sequential Quadratic Programming algorithm.

The Sequential Quadratic Programming algorithm is as follows: (1) a user defines the dose volume constraints for target and critical organs; (2) given a starting point, $x_0$, the point is passed to objective function (e.g., as shown in Equation 1 above); and (3) at each iteration, the exact problem is approximated in a linear quadratic expansion where a term involves an approximated Hessian updated using a Quasi-Newton method and the other term involves the gradient.

The following Equation 4 describes sequential quadratic programming and is as follows:

$$\min_{d \in \mathcal{R}^n} \frac{1}{2} d^T H_k d + \nabla f(x_k)^T d \quad (4)$$

$$\nabla g_i(x_k)^T d + g_i(x_k) = 0, \, i = 1, \ldots, m_e$$

$$\nabla g_i(x_k)^T d + g_i(x_k) \leq 0, \, i = m_e + 1, \ldots, m.$$

The solution is used to form a new iterate as provided by Equation 5 as follows:

$$x_k+1 = x_k + a_k d_k \quad (5).$$

The step size, $\alpha$, and direction, d, for each iterate can be produced by a trust-region method and/or by a line-search active-set or interior point methods. The Sequential Quadratic Programming algorithm may continue until the optimization reaches a minimum or is terminated by the user of the planning apparatus 102.

Figure 11:
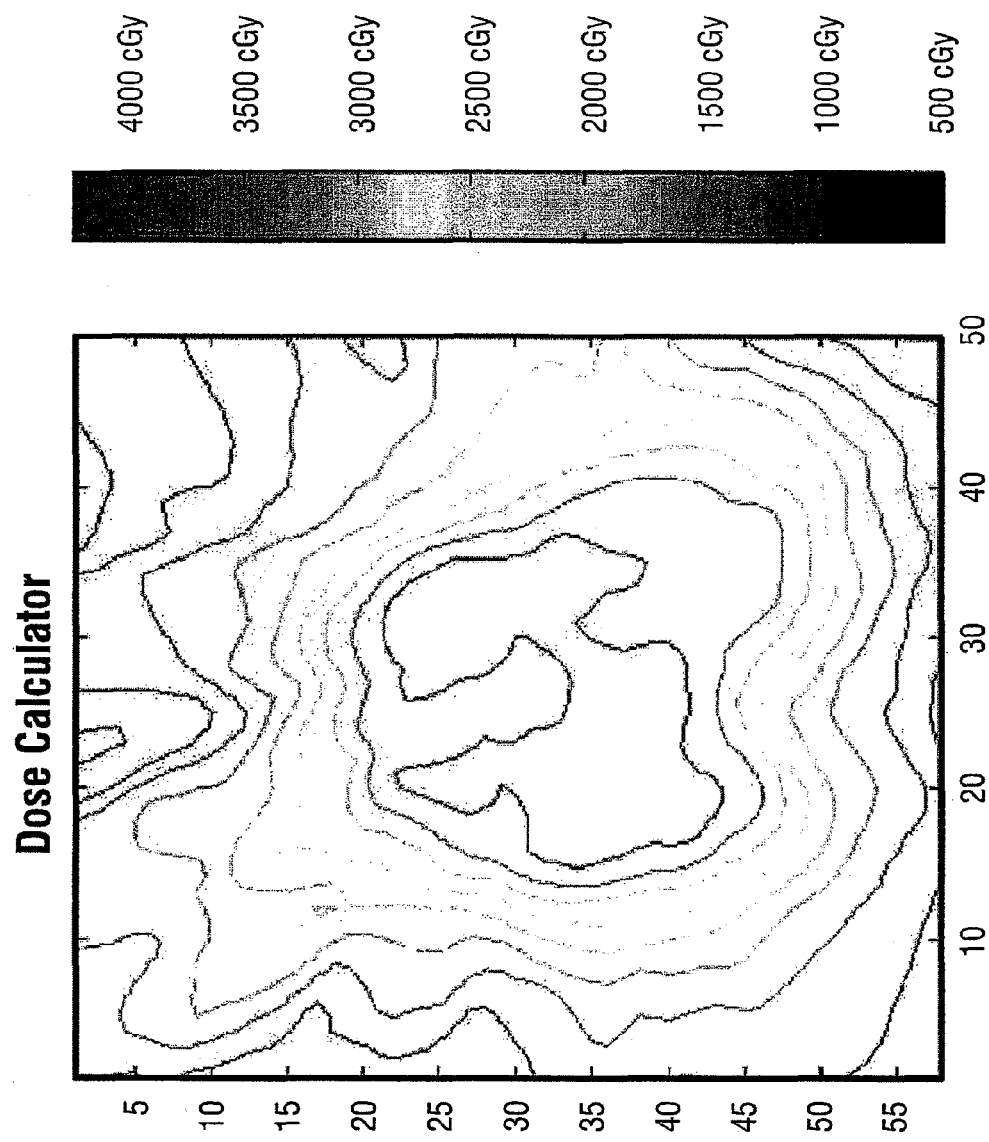
FIG. 11 shows a plot illustrating aspects of a dose calculation result generated by a radiation therapy treatment planning system in accordance with the present disclosure.
Figure 12:
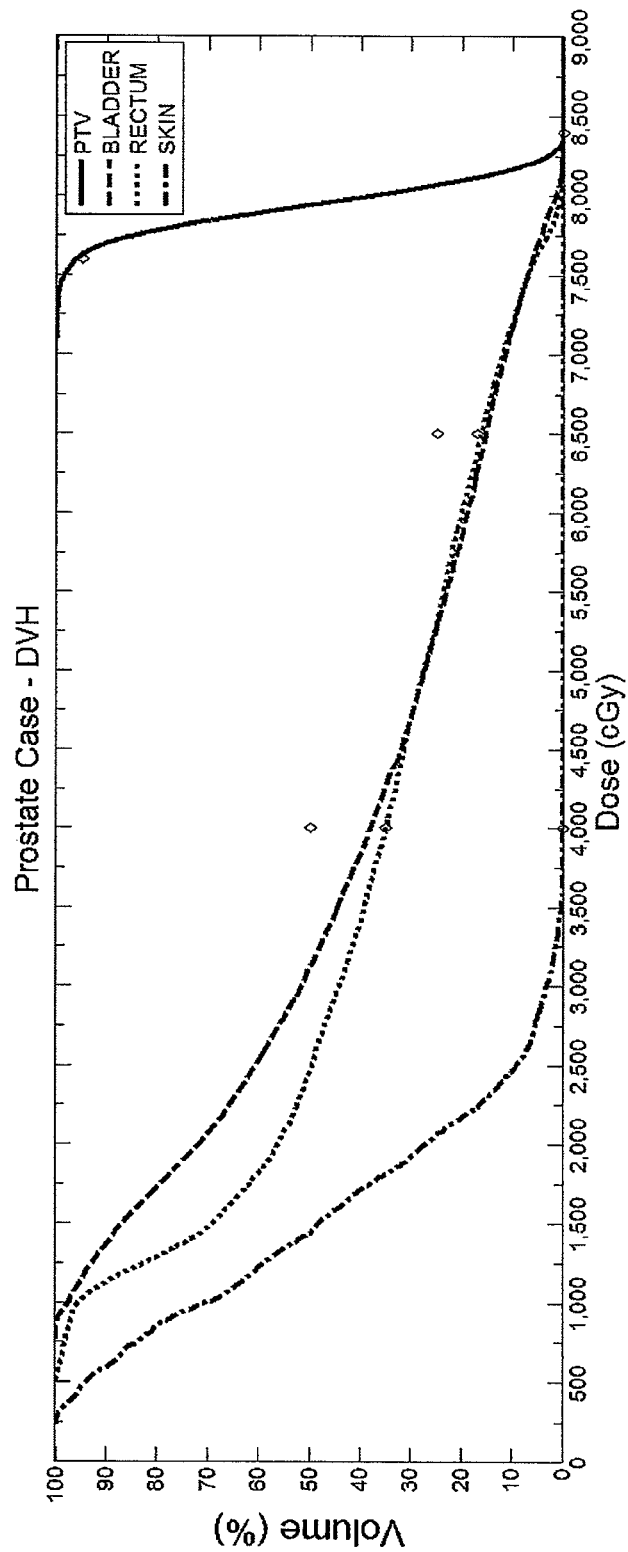
FIG. 12 illustrates a dose volume histogram corresponding to a conventionally fractionated radiotherapy treatment plan generated by a radiation therapy treatment planning system in accordance with the present disclosure.
Figure 13:
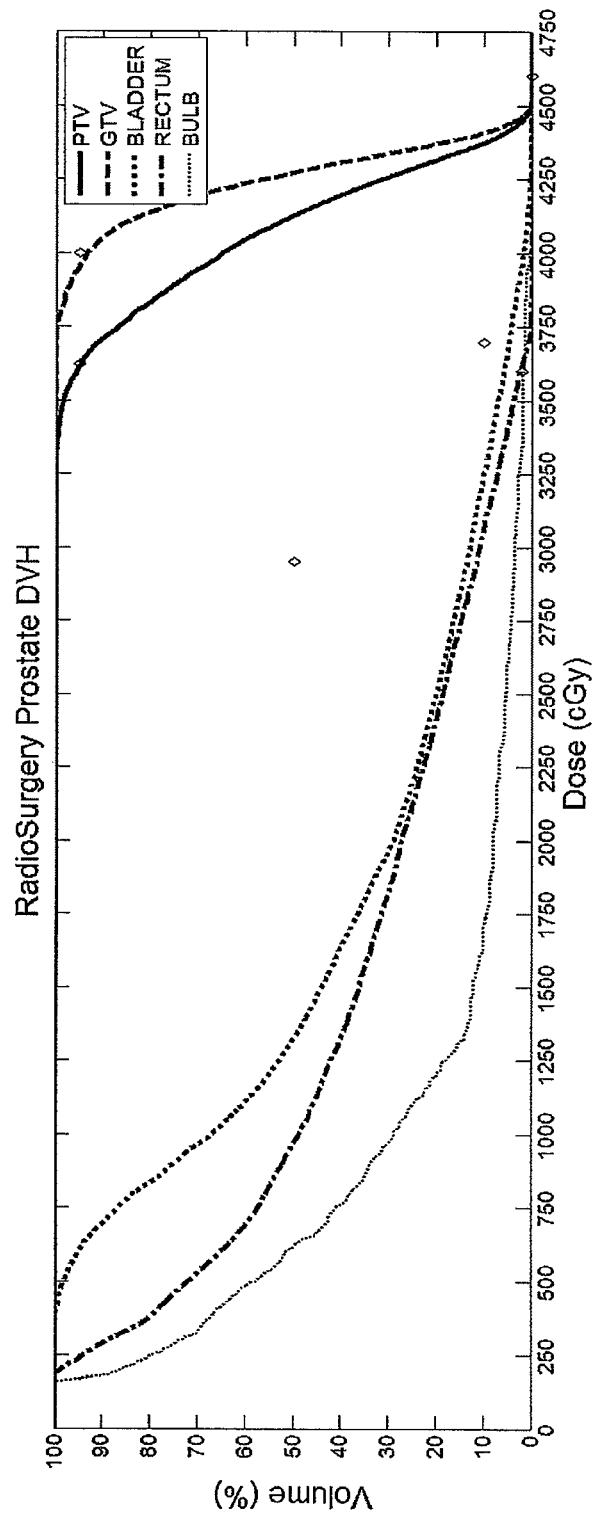
FIG. 13 illustrates a dose volume histogram corresponding to a hypofractionated radiotherapy treatment plan generated by a radiation therapy treatment planning system in accordance with the present disclosure.
Figure 14:
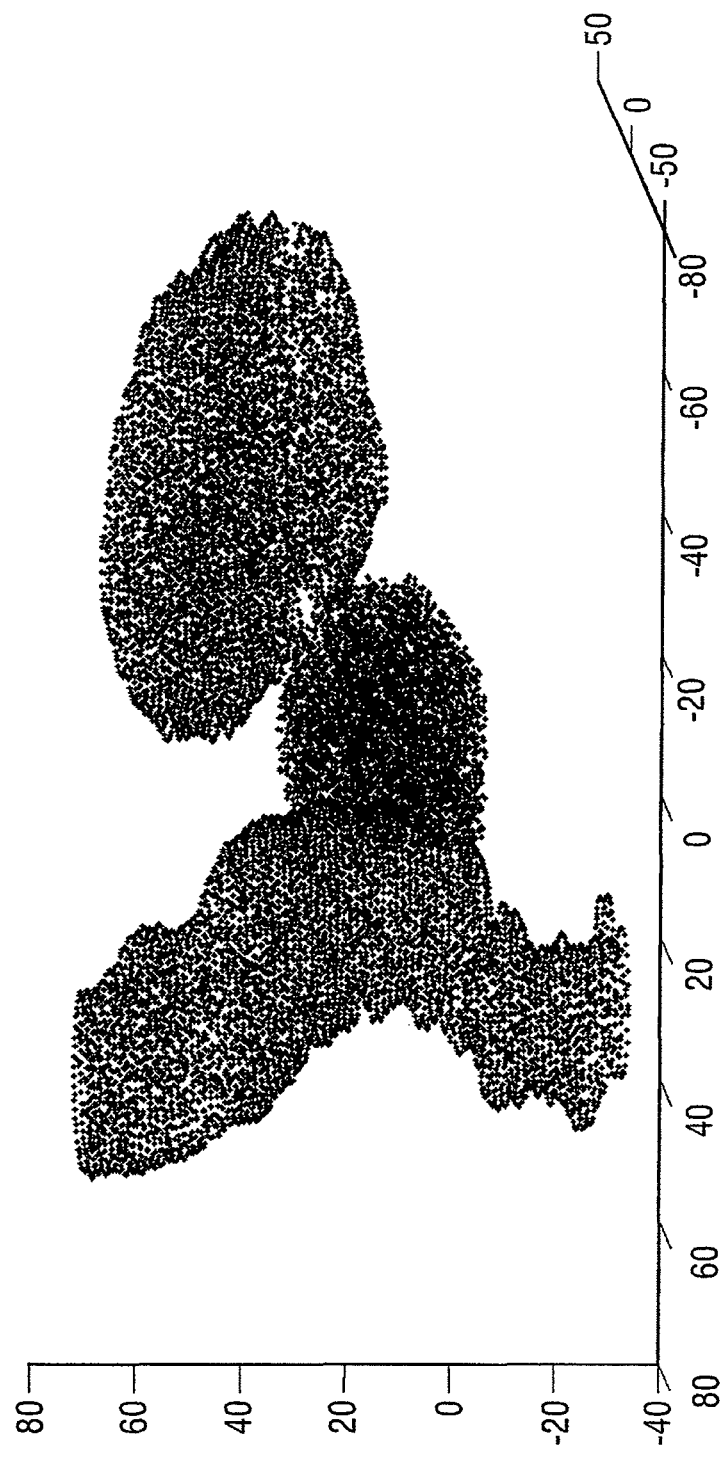
FIG. 14 illustrates a relationship between optimization points generated by a radiation therapy treatment planning system in accordance with the present disclosure.

Referring again to FIG. 1, the planning apparatus 102 includes the planning terminal 104, which may be a personal computer. The planning terminal 104 has a screen 114 capable of showing a GUI for user interaction with the radiotherapy planning component 200 of FIG. 2. FIG. 10 depicts an embodiment of a user interface of screen 114 of FIG. 1 that a user may utilize to interface with radiotherapy planning component 200 of FIG. 2. FIGS. 11-14 also show several GUI outputs of screen 114 of the planning terminal 104. FIG. 11 shows a plot illustrating aspects of a dose calculation result generated by radiation therapy treatment planning component 200 of FIG. 2. FIG. 12 illustrates a dose volume histogram corresponding to a conventionally fractionated radiotherapy treatment plan generated by radiation therapy treatment planning component 200 (see FIG. 2) while FIG. 13 illustrates a dose volume histogram corresponding to a hypofractionated radiotherapy treatment plan generated by radiation therapy treatment planning component 200 (see FIG. 2). FIG. 14 illustrates optimization points generated by the geometric representation component and passed to the radiation therapy treatment planning component 200 (see FIG. 2).

Although the present disclosure has been described in considerable detail with reference to certain preferred versions thereof, other versions are possible. For example, although a planning terminal 104 is shown as a PC, other software or hardware platforms may be utilized such as cloud computing, virtual computing, a combined radiation treatment apparatus and planning terminal, portable terminals, laptops, PDAs, touch-screen based PCs and the like. Therefore, the spirit and scope of the appended claims should not be limited to the description of the preferred versions contained therein.

What is claimed is:

1. A method of radiotherapy treatment planning, comprising:
   determining a set of beam geometry and dosimetric parameters from a totality of beams;
   calculating dose deposition coefficients responsive to the beam geometry and dosimetric parameters;
   generating a set of points corresponding to a tissue volume, wherein each of the points corresponds to a place of interaction of a beam with a tissue volume;
   identifying a solution subset of beams from the totality of beams;
   evaluating the solution based on one of an objective, fitness, or cost function; and
   activating a radiation source in accordance with the solution,
   wherein the objective function comprises a quadratic function of the form:

$$F_{fit}(\vec{x}, \vec{w}, \vec{d}, \vec{v}) = \Theta(v_{t,min} - v_{p,min})w_{t,min}\sum_{1}^{n_t}\Theta\left(\delta_{thres,min} - \sum_{1}^{b}DDC_{ij}x_j\right)\left(\sum_{1}^{b}DDC_{ij}x_j - d_{p,min}\right)^2 +$$

$$\Theta(v_{t,max} - v_{p,max})w_{t,max}\sum_{1}^{n_t}\Theta\left(\sum_{1}^{b}DDC_{ij}x_j - \delta_{thres,max}\right)\left(\sum_{1}^{b}DDC_{ij}x_j - d_{p,max}\right)^2 + \sum_{l=1}^{org}\left[\sum_{m=1}^{c_{lm}}[\Theta(v_{lm} - v_{p,lm})]w_{lm}\sum_{1}^{n_l}\Theta\left(\sum_{1}^{b}DDC_{kj}x_j - \delta_{thres,lm}\right)\left(\sum_{1}^{b}DDC_{kj}x_j - d_{p,lm}\right)^2\right].$$

2. The method of radiotherapy treatment according to claim 1, wherein identifying step is performed in accordance with at least one of population-based heuristics, population-based meta-heuristics, memes, a local search, local learning procedures, or global learning procedures.

3. The method of radiotherapy treatment according to claim 1, wherein the identifying step is performed in accordance with a population-based meta-heuristic global optimization including at least one of evolutionary computation, ant colony, swarm intelligence, neural networks, differential evolution, artificial life, cultural algorithms, harmony search, artificial immune systems, learnable evolution models, and tabu search.

4. The method of radiotherapy treatment according to claim 1, further including:
   selecting at least one parent candidate;
   combining parent candidates to generate at least one offspring solution;
   generating at least one random mutation solution;
   applying a local or global learning procedure to at least one individual solution; and
   selecting at least one survival candidate from at least one of an offspring solution, a mutation solution, or a learning procedure solution.

5. The method of radiotherapy treatment according to claim 1, further including performing a local search in the solution subset.

6. A radiotherapy system comprising:
   a planning apparatus comprising:
      at least one processor; and
      a computer-readable storage medium in communication with the at least one processor wherein the computer-readable storage medium comprises one or more programming instructions for:
         determining a set of beam geometry and dosimetric parameters from a totality of beams;
         calculating dose deposition coefficients responsive to the beam geometry and dosimetric parameters;
         generating a set of points corresponding to a tissue volume, wherein each of the points corresponds to a place of interaction of a beam with a tissue volume;
         identifying a solution subset of beams from the totality of beams; and
         evaluating the solution subset based on an objective function; and
   a radiation treatment apparatus adapted to receive the evaluated solution subset and apply radiation to a planning treatment volume in accordance with the evaluated solution subset,
   wherein the objective function comprises:

$$F_{fit}(\vec{x}, \vec{w}, \vec{d}, \vec{v}) = \Theta(v_{t,min} - v_{p,min})w_{t,min}\sum_{1}^{n_t}\Theta\left(\delta_{thres,min} - \sum_{1}^{b}DDC_{ij}x_j\right)\left(\sum_{1}^{b}DDC_{ij}x_j - d_{p,min}\right)^2 +$$

$$\Theta(v_{t,max} - v_{p,max})w_{t,max}\sum_{1}^{n_t}\Theta\left(\sum_{1}^{b}DDC_{ij}x_j - \delta_{thres,max}\right)\left(\sum_{1}^{b}DDC_{ij}x_j - d_{p,max}\right)^2 +$$

-continued $$\sum_{l=1}^{org}\left[\sum_{m=1}^{c_{lm}}[\Theta(v_{lm}-v_{p,lm})]w_{lm}\sum_{1}^{n_l}\Theta\left(\sum_{1}^{b}DDC_{kj}x_j-\delta_{thres,lm}\right)\left(\sum_{1}^{b}DDC_{kj}x_j-d_{p,lm}\right)^2\right].$$

7. The radiotherapy system according to claim 6, wherein the one or more programming instructions for identifying is performed in accordance with at least one of population-based heuristics, population-based meta-heuristics, memes, local search, local learning procedures, or global learning procedures.

8. The radiotherapy system according to claim 6, wherein the one or more programming instructions for identifying is performed in accordance with a population-based meta-heuristic global optimization including at least one of evolutionary computation, ant colony, swarm intelligence, neural networks, differential evolution, artificial life, cultural algorithms, harmony search, artificial immune systems, learnable evolution models, or tabu search.

9. The radiotherapy system according to claim 6, wherein the one or more programming instructions further comprises:
selecting at least one parent candidate;
combining parent candidates to generate at least one offspring solution;
generating at least one random mutation solution;
applying a local or global learning procedure to at least one individual solution; and
selecting at least one survival candidate from at least one of an offspring solution, a mutation solution, or a learning procedure solution.

10. The radiotherapy system according to claim 6, wherein the one or more programming instructions further comprises performing a local search in the solution subset utilizing at least one of conjugate gradient, a gradient method and linear programming.

11. A radiotherapy planning system comprising:
at least one processor; and
machine-readable media comprising a set of executable instructions adapted for execution on the one or more processors, the set of executable instructions for performing radiotherapy planning comprises:
receiving a first dose-volume constraint for a planning treatment volume;
receiving a second dose-volume constraint for tissue outside of the planning treatment volume;
determining a set of beam properties for a plurality of beams using a population-based heuristic approximation in accordance with the first and second dose-volume constraints;
refining the set of beam properties for the plurality of beams using a deterministic local trajectory search; and
generating a set of instructions to instruct a radiation treatment apparatus to apply radiation to the planning treatment volume in accordance with the plurality of beams having the refined set of beam properties,
wherein the set of executable instructions further includes instructions for evaluating a beam property of the set of beam properties for a beam of the plurality of beams using:

$$F_{fit}(\vec{x},\vec{w},\vec{d},\vec{v})=\Theta(v_{t,min}-v_{p,min})w_{t,min}\sum_{1}^{n_t}\Theta\left(\delta_{thres,min}-\sum_{1}^{b}DDC_{ij}x_j\right)\left(\sum_{1}^{b}DDC_{ij}x_j-d_{p,min}\right)^2+$$

$$\Theta(v_{t,max}-v_{p,max})w_{t,max}\sum_{1}^{n_t}\Theta\left(\sum_{1}^{b}DDC_{ij}x_j-\delta_{thres,max}\right)\left(\sum_{1}^{b}DDC_{ij}x_j-d_{p,max}\right)^2+$$

$$\sum_{l=1}^{org}\left[\sum_{m=1}^{c_{lm}}[\Theta(v_{lm}-v_{p,lm})]w_{lm}\sum_{1}^{n_l}\Theta\left(\sum_{1}^{b}DDC_{kj}x_j-\delta_{thres,lm}\right)\left(\sum_{1}^{b}DDC_{kj}x_j-d_{p,lm}\right)^2\right].$$

12. The radiotherapy planning system according to claim 11, wherein the radiation treatment apparatus includes a control system adapted to receive the set of instructions and control the radiation treatment apparatus in accordance with the set of instructions thereby applying the radiation to the planning treatment volume in accordance with the set of instructions.

13. The radiotherapy planning system according to claim 11, wherein the population-based heuristic approximation is a population-based meta-heuristic global optimization.

14. The radiotherapy planning system according to claim 13, wherein the population-based meta-heuristic global optimization includes at least one of evolutionary computation, ant colony, swarm intelligence, neural networks, differential evolution, artificial life, cultural algorithms, harmony search, artificial immune systems, learnable evolution models, or tabu search.

15. A radiotherapy treatment planning system, comprising:
a processor means for executing a set of instructions for radiation treatment planning;
a storage means for storing the set of instructions;
a parameterization means for determining geometry and dosimetric parameters for a radiation beam directed to a treatment tissue volume;
a geometric point representation means for selecting a point of the treatment tissue volume;
an evaluation means for evaluating the geometry and dosimetric parameters directed to the point of the treatment tissue volume based on an objective function; and
a heuristic means for heuristically determining a treatment plan in accordance with the evaluation of the geometry and dosimetric parameters,
wherein the objective function comprises:

$$F_{fit}(\vec{x},\vec{w},\vec{d},\vec{v})=\Theta(v_{t,min}-v_{p,min})w_{t,min}\sum_{1}^{n_t}\Theta\left(\delta_{thres,min}-\sum_{1}^{b}DDC_{ij}x_j\right)\left(\sum_{1}^{b}DDC_{ij}x_j-d_{p,min}\right)^2+$$

-continued $$\Theta(v_{t,max} - v_{p,max})w_{t,max} \sum_{1}^{n_t} \Theta\left(\sum_{1}^{b} DDC_{ij}x_j - \delta_{thres,max}\right)\left(\sum_{1}^{b} DDC_{ij}x_j - d_{p,max}\right)^2 +$$

$$\sum_{l=1}^{org}\left[\sum_{m=1}^{c_{lm}}[\Theta(v_{lm} - v_{p,lm})]w_{lm}\sum_{1}^{n_l}\Theta\left(\sum_{1}^{b}DDC_{kj}x_j - \delta_{thres,lm}\right)\left(\sum_{1}^{b}DDC_{kj}x_j - d_{p,lm}\right)^2\right].$$

16. The radiotherapy treatment planning system according to claim 15, further comprising a truncation means for truncating a beam of the treatment plan.

17. The radiotherapy treatment planning system according to claim 15, further comprising a local search means for optimizing a beam of the treatment plan.

18. The radiotherapy treatment planning system according to claim 15, further comprising a radiation means for irradiating the treatment tissue volume in accordance with the treatment plan.

* * * * *